United States Patent
Schneider et al.

(10) Patent No.: US 12,065,677 B2
(45) Date of Patent: *Aug. 20, 2024

(54) METHOD FOR THE FERMENTATIVE PRODUCTION OF GUANIDINOACETIC ACID

(71) Applicant: Evonik Operations GmbH, Essen (DE)

(72) Inventors: Frank Schneider, Halle (DE); Frank Jankowitsch, Sassenberg (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/004,327

(22) PCT Filed: Jun. 28, 2021

(86) PCT No.: PCT/EP2021/067676
§ 371 (c)(1),
(2) Date: Jan. 5, 2023

(87) PCT Pub. No.: WO2022/008280
PCT Pub. Date: Jan. 13, 2022

(65) Prior Publication Data
US 2023/0227795 A1    Jul. 20, 2023

(30) Foreign Application Priority Data
Jul. 9, 2020  (EP) ..................... 20184949

(51) Int. Cl.
*C12N 9/10*  (2006.01)
*C12P 13/04*  (2006.01)

(52) U.S. Cl.
CPC ......... *C12N 9/1003* (2013.01); *C12N 9/1096* (2013.01); *C12P 13/04* (2013.01); *C12Y 201/04001* (2013.01); *C12Y 206/01002* (2013.01); *C12Y 206/01004* (2013.01); *C12Y 206/01044* (2013.01)

(58) Field of Classification Search
CPC ...... C12N 9/1003; C12N 9/1096; C12P 13/04
See application file for complete search history.

(56) References Cited

U.S. PATENT DOCUMENTS

| 11,384,369 B2 * | 7/2022 | Koch ............. C12P 13/04 |
| 2005/0188435 A1 | 8/2005 | Igarashi et al. |
| 2007/0031946 A1 | 2/2007 | Suga et al. |
| 2019/0185888 A1 | 6/2019 | Koepke et al. |

FOREIGN PATENT DOCUMENTS

| CN | 106065411 | 11/2016 |
| CN | 110904018 | 3/2020 |
| CN | 111748506 | 10/2020 |
| EP | 3 153 573 | 4/2017 |
| WO | 2018/079687 | 5/2018 |
| WO | 2020/163935 | 8/2020 |
| WO | 2022/008276 | 1/2022 |
| WO | 2022/008280 | 1/2022 |
| WO | 2022/243116 | 11/2022 |

OTHER PUBLICATIONS

Muenchhoff. A novel prokaryotic L-arginine:glycine amidinotransferase is involved in cylindrospermopsin biosynthesis. FEBS J. Sep. 2010;277(18):3844-60.*
A0A418GIW9_ECOLX. UnitProtKB/TrEMBL Database. May 8, 2019.*
English translation CN 116065411. Retrieved on May 22, 2023.*
Stewart. Biotechnology and Genetic Engineering Reviews, 14:67-143, 1997.*
A0A1D8TKD3_9CYAN. UniProtKB/TrEMBL Database. May 2019.*
GGT1_ARATH. UniProtKB/Swiss-Prot Database. Jun. 2019.*
English translation CN 106065411. Retrieved on May 22, 2023.*
Extended European Search Report received for European Patent Application No. 20184949.4, mailed on Jan. 19, 2021, 5 pages.
Ginesy et al., "Metabolic engineering of *Escherichia coli* for enhanced arginine biosynthesis", Microbial Cell Factories, vol. 14, Issue 29, 2015, pp. 1-11.
Guthmiller et al., "Cloning and Sequencing of Rat Kidney L-Arginine:Glycine Amidinotransferase", The Journal of Biological Chemistry, vol. 269, No. 26, Jul. 1, 1994, pp. 17556-17560.
Humm et al., "Recombinant expression and isolation of human L-arginine:glycine amidinotransferase and identification of its active-site cysteine residue", Biochemical Journal, vol. 322, 1997, pp. 771-776.
International Search Report dated Oct. 14, 2021, in PCT/EP2021/067676, 8 pages.
Kameya et al. "Purification of three aminotransferases from Hydrogenobacter thermophilus TK-6-novel types of alanine or glycine aminotransferase enzymes and catalysis", The Febs Journal, vol. 277, 2010, pp. 1876-1885.
Liepman et al., "Alanine aminotransferase homologs catalyze the glutamate: Glyoxylate aminotransferase reaction in peroxisomes of *Arabidopsis*", Plant Physiology, American Society of Plant Biologists, vol. 131, Jan. 2003, pp. 215-227.
Muenchhoff et al., "Identification of two residues essential for the stringent substrate specificity and active site stability of the prokaryotic L-arginine:glycine amidinotransferase CyrA", The Febs Journal, vol. 279, 2012, pp. 805-815.
Park et al., "Metabolic engineering of Corynebacterium glutamicum for L-arginine production", Nature Commmicatioms, vol. 5, No. 4618, Aug. 2014, pp. 1-9.
Sakuraba et al., "Novel Archaeal Alanine: Glyoxylate Aminotransferase from Thermococcus litoralis", Journal of Bacteriology, vol. 186, No. 15, Aug. 2004, pp. 5513-5518.

(Continued)

*Primary Examiner* — Yong D Pak
(74) *Attorney, Agent, or Firm* — Grüneberg and Myers PLLC

(57) ABSTRACT

A microorganism is transformed to be capable of producing guanidinoacetic acid (GAA). A method can be used for the fermentative production of GAA using such a microorganism. A corresponding method can be used for the fermentative production of creatine.

28 Claims, No Drawings
Specification includes a Sequence Listing.

(56) References Cited

OTHER PUBLICATIONS

Salusjärvi et al., "Biotechnological production of glycolic acid and ethylene glycol: current state and perspectives", Applied Microbiology and Biotechnology, vol. 103, Feb. 2019, pp. 2525-2535.

Sosio et al., "Analysis of the Pseudouridimycin Biosynthetic Pathway Provides Insights into the Formation of C-nucleoside Antibiotics", Cell Chemical Biology, vol. 25, May 2018, pp. 540-549.

Takada et al., "Characteristics of alanine: glyoxylate aminotransferase from *Saccharomyces cerevisiae*, a regulatory enzyme in the glyoxylate pathway of glycine and serine biosynthesis from tricarboxylic acid-cycle intermediates", Biochemical Journal, vol. 231, 1985, pp. 157-163.

Wang et al., "Increasee expression of pyruvate carboxylase and biotin protein ligase increases lysine production in a biotin prototrophic Corynebacterium glutamicum strain", Engineering in Life Sciences, vol. 15, 2015, pp. 73-82.

Written Opinion dated Oct. 14, 2021, in PCT/EP2021/067676, 9 pages.

Yim et al., "Purification and characterization of an arginine regulatory protein, ArgR, in Corynebacterium glutamicum", Journal of Industrial Microbiology and Biotechnology, vol. 38, 2011, pp. 1911-1920.

Zahoor et al., "Metabolic engineering of Corynebacterium glutamicum for glycolate production", Journal of Biotechnology, vol. 192, 2014, pp. 366-375.

Zhang et al., "Reconstitution of the ornithine cycle with arginine: Glycine amidinotransferase to engineer *Escherichia coli* into an efficient whole-cell catalyst of guanidinoacetate", ACS Synthetic Biology, vol. 9, 2020, pp. 2066-2075.

U.S. Appl. No. 17/757,441, filed Jun. 15, 2022, Schenider et al.

Schneider et al., U.S. Appl. No. 18/004,364, filed Jan. 5, 2023.

U.S. Appl. No. 18/004,364, filed Jan. 5, 2023, Schneider et al.

Extended Search Report received for European Patent Application No. 20184966.8, mailed on Jan. 19, 2021, 5 pages.

International Search Report mailed on Oct. 14, 2021, for PCT Application No. PCT/EP2021/067647, 8 pages.

Written Opinion mailed on Oct. 14, 2021, for PCT Application No. PCT/EP2021/067647, 9 pages.

Zhang et al., "Reconstitution of the ornithine cycle with arginine: Glycine amidinotransferase to engineer *Escherichia coli* into an efficient whole-cell catalyst of guanidinoacetate", ACS Synthetic Biology, Just accepted manuscript, downloaded from pubs.acs.org on Aug. 3, 2020, 22 pages.

Eurasian Office Action dated Mar. 1, 2024, in Eurasian Application No. 202390301, 4 pages.

European Communication pursuant to Article 94(3) EPC, dated Feb. 19, 2024, in European Application No. 21736601.2, 7 pages.

French, et al. "What is a Conservative Substitution?", Journal of Molecular, Evolution, vol. 19, 1983, pp. 171-175.

Genbank, Accession No. AOW98079.1, "Glycine amidinotransferase [ Moorena producens PAL-8-15-08-1]", 2019, 2 pages. https://www.ncbi.nlm.nih.gov/protein/AOW98079.1.

Ledwidge et al., "The Dual Biosynthetic Capability of N-Acetylornithine Aminotransferase in Arginine and Lysine Biosynthesis", Biochemistry, vol. 38, 1999, pp. 3019-3024.

Park et al., "Metabolic engineering of Corynebacterium glutamicum for L-argine production", Nature Communications, vol. 5, 4618, 2014, pp. 1-9.

William R. Pearson, "An Introduction to Sequence Similarity ("Homology") Searching", Current Protocols Bioinformatics, 3.1.1-3.1.8, Jun. 2013, 9 pages.

Uniprot, Accession No. Q9C4M4, 2019, 2 pages, www.uniprot.org.

U.S Office Action dated Sep. 8, 2023, in U.S. Appl. No. 18/004,364, 23 pages.

\* cited by examiner

METHOD FOR THE FERMENTATIVE PRODUCTION OF GUANIDINOACETIC ACID

CROSS-REFERENCE TO RELATED APPLICATIONS

This application Is the National Stage entry under § 371 of International Application No. PCT/EP2021/087878, filed on Jun. 28, 2021, and which claims the benefit of priority to European Application No. 20184949.4, filed on Jul. 9, 2020. The content of each of these applications is hereby incorporated by reference in its entirety.

REFERENCE TO SEQUENCE LISTING

The present application is accompanied by an ASCII text file as a computer readable form containing the sequence listing entitled, "004790USPCT_SL_ST25.txt", created on Oct. 21, 2022, with a file size of 54,999 bytes, the content of which is hereby Incorporated by reference in its entirety.

BACKGROUND OF THE INVENTION

Field of the Invention

The present invention relates to a microorganism transformed to be capable of producing guanidinoacetic acid (GAA) and to a method for the fermentative production of GAA using such microorganism. The present invention also relates to a method for the fermentative production of creatine.

Description of Related Art

GAA is an organic compound used as animal feed additive (US2011257075 A1). GAA is a natural precursor of creatine (e.g. Humm et al., Biochem. J. (1997) 322, 771-776). Therefore, the supplementation of GAA allows for an optimal supply of creatine in the organism.

The present invention pertains to a method to produce GAA by a fermentative process using industrial feed stocks (e.g. ammonia, ammonium salts and glucose or sugar containing substrates) as starting material. In biological systems GAA and L-ornithine are formed from arginine and glycine as starting materials by the catalytic action of an L-arginine: glycine-amidinotransferase (AGAT; EC 2.1.4.1), which is the first step in creatine biosynthesis:

Guthmler et al. (J Biol Chem. 1994 July 1269(26):17558-80) have characterized a rat kidney AGAT by cloning and heterologously expressing the enzyme in *Escherichia coli* (*E. coli*). Muenchhoff et al. (FEBS Journal 277 (2010) 3844-3880) report the first characterization of an AGAT from a prokaryote also by cloning and heterologously expressing the enzyme in *E. coli*. Sosio et al. (Cell Chemical Biology 25, 540-549, May 17, 2018) elucidated the biosynthetic pathway for pseudouridimycin in *Streptomyces* sp. They describe as an intermediate reaction the formation of GAA and L-ornithine by the reaction of L-arginine with glycine catalyzed by PumN, an L-arginine:glycine-amidinotransferase (AGAT).

Several approaches for increasing the production of one of the starting materials in GAA synthesis, i.e. L-arginine, in microorganisms, particularly bacteria, are also known from literature. An overview for the metabolic engineering of *Corynebacterium glutamicum* (*C. glutamicum*) for L-arginine production is provided by Park et al. (NATURE COMMUNICATIONS|DOI: 10.1038/ncomms5818). They propose random mutagenesis and screening for L-arginine producers of already L-arginine producing *C. glutamicum* strains, e.g. of ATCC 21831 (Nakayama and Yoshida 1974, U.S. Pat. No. 3,849,250 A) and stepwise rational metabolic engineering based on system-wide analysis of metabolism results in a gradual increase in L-arginine production throughout the strain engineering steps. Yim et al. (J Ind Microbiol Biotechnol (2011) 38:1911-1920) could show that inactivation of the argR, gene coding for the central repressor protein ArgR controlling the L-arginine biosynthetic pathway, by disrupting the chromosomal argR gene in *C. glutamicum* leads to an improved arginine-producing strain. Ginesy et al. (Microbial Cell Factories (2015) 14:29) report the successful engineering of *E. coli* for enhanced arginine production. Among other, they proposed the deletion of the argR repressor gene.

A method of using a genetic recombinant strain, wherein a gene which inhibits the expression of arginine-biosynthesizing operon argR was inactivated has been reported by Suga et al. (US20070031948 A1). In particular, the deletion in argR, which controls the arginine operon, has been considered as an important factor in arginine production.

Fan Wenchao discloses a method for the production of creatine by fermentation of non-pathogenic microorganisms, such as *C. glutamicum* (CN108085411 A). The microorganism has the following biotransformation functions: glucose conversion to L-glutamic acid; conversion of L-glutamic acid to N-acetyl-L-glutamic acid; conversion of N-acetyl-L-glutamic acid to N-acetyl-L-glutamic acid semialdehyde; conversion of N-acetyl-L-glutamic acid semialdehyde to N-acetyl-L-omithine; conversion of N-acetyl-L-omithine to L-ornithine; conversion of L-ornithine to L-citrulline; conversion of L-citruline to arginino-succinic acid; conversion of arginino-succinic acid to L-arginine; conversion of L-arginine to guanidinoacetic acid; and, finally, conversion of guanidinoacetic acid to creatine. Fan Wenchao proposes, that the microorganism overexpresses one or more enzymes selected from the group consisting of N-acetylglutamate-synthase, N-acetylornithine-5-aminotransferase, N-acetylornithinase, omithine-carbamoyl transferase, argininosuccinate synthetase, glycine amidino-transferase (EC: 2.1. 4.1), and guanidinoacetate N-methyltransferase (EC: 2.1.1.2). The microorganism overexpresses preferably glycine amidinotransferase (L-arginine:glycine amidinotransferase) and guanidinoacetate N-methyltransferase.

As to the second starting material of the GAA biosynthesis, K would be desirable increasing the provision of glycine in order to improve the GAA biosynthesis in microorganisms that are naturally provided with a homologous gene coding for a protein having the function of a L-arginine: glycine amidinotransferase (AGAT) or have been provided with a heterologous gene coding for a protein having the function of a L-arginine:glycine amidinotransferase (AGAT).

The so called glyoxylate shunt pathway, naturally occurring in microorganisms, such as *E. coli* or *C. glutamicum*, is a side reaction of the tri-carbonic acid (TCA) cycle (Krebs cycle) and includes the formation of glyoxylate and succinate from isocitrate by isocitrate lyase and the formation of malate from glyoxylate and acetyl-CoA by malate synthase (Salusjärvi et al., Applied Microbiology and Biotechnology (2019) 103:2525-2535).

Glyoxylate may be used as starting material for the formation of glycine in the presence of an amino donor, such as amino acids, and a glyoxylate transaminase. Glyoxylate transaminases catalyze the transfer of an amino group from an amino acid to glyoxylate. The products of this transfer are glycine and the corresponding α-keto acid.

In an attempt to improve the production of glycolate in *C. glutamicum* Zahoor et al. (Journal of Biotechnology 192 (2014) 366-375) achieved an increase in the supply of the glyoxylate precursor among others by the deletion of the malate synthase gene aceB.

Several glyoxylate amino transferases are known and vary in their substrate specificity with respect to the amino donor (cf. e.g. Kameya at al. FEBS Journal 277 (2010) 1876-1885; Liepman and Olsen, Plant Physiol. Vol. 131, 2003, 215-227; Sakuraba et al., JOURNAL OF BACTERIOLOGY, August 2004, p. 5513-5518; Takada and Noguchi, Biochem. J. (1985) 231, 157-163). Since most of these glyoxylate aminotransferase are able to use different amino acids as amino donors, they are often annotated with different EC numbers. However, al these aminotransferases have in common that they use glyoxylate as acceptor molecule, or, in case of the reverse reaction, glycine as donor molecule.

Examples for a protein having the function of a glyoxylate aminotransferase are the following:

Glycine transaminase (EC 2.6.1.4) catalyzes the reaction:

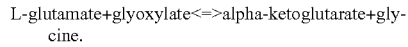
L-glutamate+glyoxylate<=>alpha-ketoglutarate+glycine.

Glycine:oxaloacetate transaminase (EC 2.6.1.35) catalyzes the reaction:

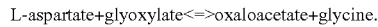
L-aspartate+glyoxylate<=>oxaloacetate+glycine.

Alanine:glyoxylate transaminase (EC 2.6.1.44) catalyzes the reaction:

L-alanine+glyoxylate<=>pyruvate+glycine.

Serine:glyoxylate transaminase (EC 2.6.1.45) catalyzes the reaction:

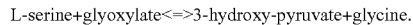
L-serine+glyoxylate<=>3-hydroxy-pyruvate+glycine.

Methionine:glyoxylate transaminase (EC 2.6.1.73) catalyzes the reaction:

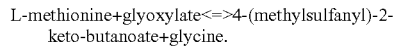
L-methionine+glyoxylate<=>4-(methylsulfanyl)-2-keto-butanoate+glycine.

The aromatic amino acid:glyoxylate transaminase (EC 2.6.1.60) catalyzes the reaction:

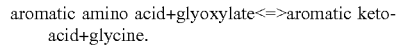
aromatic amino acid+glyoxylate<=>aromatic keto-acid+glycine.

Kynurenine:glyoxylate transaminase (EC 2.6.1.63) catalyzes the reaction:

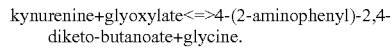
kynurenine+glyoxylate<=>4-(2-aminophenyl)-2,4-diketo-butanoate+glycine.

(S)-Ureido-glycine:glyoxylate transaminase (EC 2.6.1.112) catalyzes the reaction:

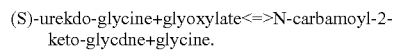
(S)-urekdo-glycine+glyoxylate<=>N-carbamoyl-2-keto-glycdne+glycine.

However, until now no endogenous glyoxylate aminotransferases have been described for *E. coli* and for *C. glutamicum*. Furthermore, microorganisms suitable for an increased production of GAA compared to their wildtype forms and a respective method for the production of GAA using such microorganisms have not been reported.

SUMMARY OF THE INVENTION

Therefore, the problem underlying the present invention is to provide a microorganism transformed to be capable of producing guanidinoacetic acid (GAA), in particular a microorganism with an improved capacity of providing glycine as starting material of the GAA biosynthesis, and to a method for the fermentative production of GAA using such microorganism.

The problem is solved by a microorganism comprising at least one gene coding for a protein having the function of a L-arginine:glycine amidiotransferase (AGAT, e.g. EC 2.1.4.1) and comprising at least one protein having the function of a glyoxylate aminotransferase.

DETAILED DESCRIPTION OF THE INVENTION

Preferably, in the microorganism according to the present invention the enzymic activity of at least one protein having the function of a glyoxylate aminotransferase is increased compared to the respective enzymic activity in the wildtype microorganism.

The microorganism according to the present invention may comprise at least one gene encoding a protein having the enzymic activity of a glyoxylate aminotransferase. At least one protein having the enzymic activity of a glyoxylate aminotransferase may be homologous or heterologous.

Preferably, at least one gene encoding the protein having the enzymic activity of a glyoxylate aminotransferase is overexpressed in the microorganism of the present invention.

Preferably, the microorganism of the present invention microorganism has an increased ability to produce L-arginine compared with the ability of the wildtype microorganism.

In the context of the present invention, a microorganism having an increased ability to produce L-arginine means a microorganism producing L-arginine in excess of its own need. Examples for such L-arginine producing microorganisms are e.g. *C. glutamicum* ATCC 21831 or those disclosed by Park at al. (NATURE COMMUNICATIONS|DOI: 10.1038/ncomms5818) or by Ginesy at al. (Microbial Cell Factories (2015) 14:29).

In a particular embodiment of the present invention, the microorganism has an increased activity of an enzyme having the function of a carbamoylphosphate synthase (EC 6.3.4.16) compared to the respective enzymic activity in the wildtype microorganism.

The activity of an enzyme having the function of an argininosuccinate lyase (E.C. 4.32.1) in the microorganism according to the present invention may be increased compared to the respective enzymic activity in the wildtype microorganism.

Furthermore, in the microorganism according to the present invention, the activity of an enzyme having the function of an omithine carbamoyltransferase (EC 2.1.3.3) may be increased compared to the respective enzymic activity in the wildtype microorganism.

In the microorganism according to the present invention, the activity of an enzyme having the function of an argininosuccinate synthetase (E.C. 6.3.4.5) may be also increased compared to the respective enzymic activity in the wildtype microorganism.

Increased enzyme activities in microorganisms can be achieved, for example, by mutation of the corresponding endogenous gene. A further measure to increase enzymic activities may be to stabilize the mRNA coding for the enzymes. The increased activities of the above-mentioned enzymes may also be achieved by overexpressing the genes coding for the respective enzymes.

In a further embodiment of the microorganism according to the present invention the activity of a protein having the function of a malate synthase is decreased compared to the respective activity in the wildtype microorganism.

The activity of a protein having the function of a malate synthase may be decreased by mutating the protein to a protein having less enzymic activity than the wildtype protein, by attenuating the expression of a gene encoding the enzyme having the function of a malate synthase compared to the expression of the respective gene in the wildtype microorganism, by decreasing the efficiency of translation, e.g. by changing an ATG start codon to GTG, by introducing secondary structures into the 5' untranslated region of the mRNA or by attenuating the codon usage or by deleting the gene encoding the enzyme having the function of a malate synthase.

The microorganism according to the present invention preferably also comprises at least one or more overexpressed genes selected from the group consisting of a gene (e.g. argF/argF2/argI) coding for a protein having the function of an ornithine carbamoyltransferase (EC 2.1.3.3), a gene (e.g. argG) coding for a protein having the function of an argininosuccinate synthetase (E.C. 6.3.4.5), and a gene (e.g. argH) coding for a protein having the function of an argininosuccinate lyase (E.C. 4.3.2.1).

Furthermore, in the microorganism according to the present invention the arginine operon (argCJBDFR) may be overexpressed.

Alternatively, in the microorganism according to the present invention the argR gene coding for the arginine responsive repressor protein ArgR may be attenuated or deleted.

In a further embodiment of the present invention and, optionally in addition to the above-mentioned modifications, at least one or more of the genes coding for an enzyme of the biosynthetic pathway of L-arginine, comprising of gdr, argJ, argB, argC and/or argD coding for a glutamate dehydrogenase, an ornithine acetyltransferase, an acetylglutamate kinase, an acetylglutamylphosphate reductase and an acetylornithine aminotransferase, respectively, is overexpressed in the microorganism according to the present invention.

Table 1 shows the different names of enzymes involved in or contributing to arginine biosynthesis in different species, i.e. *E. coli*, *C. glutamicum* and *Pseudomonas putida* (*P. putida*).

TABLE 1

Names of Enzymes

| Enzyme name | Alias | EC Number | E. coli | C. glutamicum | P. putida |
|---|---|---|---|---|---|
| glutamate dehydrogenase | NADP-SPECIFIC GLUTAMATE DEHYDROGENASE | 1.4.1.4 (1.4.1.2 in *P. putida*) | gdhA | gdh | gdhA/gdhB |
| N-acetyl glutamokinase | ACETYLGLUTAMATE KINASE | 2.7.2.8 | argB | argB | argB |
| N-acetylglutamyl phosphate reductase | N-acetyl-gamma-glutamylphosphate reductase | 1.2.1.38 | argC | argC | argC |
| N-acetylglutamic acid-γ-semialdehyde dehydrogenase | ACETYLORNITHINE AMINOTRANSFERASE (in e.c. bifunctional acetylornithine aminotransferase/ succinyldiaminopimelate aminotransferase) | 2.6.1.11/ 2.6.1.17 | argD | argD | aruC |
| acetylornithine deacetylase | bifunctional acetylornithine deacetylase/GLUTAMATE N-ACETYLTRANSFERASE | 2.3.1.35/ 2.3.1.1 | | argJ | argJ |
| acetylornithine deacetylase | | 3.5.1.16 | argE | | argE |
| | GLUTAMATE N-ACETYLTRANSFERASE | 2.3.1.1 | argA | | argA |
| ornithine carbamoyltransferase | ornithine carbamoyltransferase 1 | 2.1.3.3 | argI | argF/argF2 | arcB/argF |
| Argininosuccinate synthetase | ARGININOSUCCINATE SYNTHASE | 6.3.4.5 | argG | argG | argG |
| Argininosuccinate lyase | ARGININOSUCCINATE LYASE | 4.3.2.1 | argH | argH | argH |
| carbamoyl-phosphate synthase | carbamoyl-phosphate synthase | 6.3.5.5 | carAB | carAB | carAB |
| carbamate kinase | carbamate kinase | 2.7.2.2 | ybcF/yqeA | | arcC |

Overexpression of a gene is generally achieved by increasing the copy number of the gene and/or by functionally linking the gene with a strong promoter and/or by enhancing the ribosomal binding site and/or by codon usage optimization of the start codon or of the whole gene or a combination comprising a selection of or all methods mentioned above.

In a further embodiment of the present invention of the microorganism of the present invention the gene coding for a protein having the function of an L-arginine:glycine amidinotransferase is heterologous.

A heterologous gene means that the gene has been inserted into a host organism which does not naturally have this gene. Insertion of the heterologous gene in the host is performed by recombinant DNA technology. Microorganisms that have undergone recombinant DNA technology are called transgenic, genetically modified or recombinant.

A heterologous protein means a protein that is not naturally occurring in the microorganism.

A homologous or endogenous gene means that the gene including its function as such or the nucleotide sequence of the gene is naturally occurring in the microorganism or is "native" in the microorganism.

A homologous or a native protein means a protein that is naturally occurring in the microorganism.

Proteins having the function of an L-arginine:glycine amidinotransferase (AGAT) belong to the amidinotransferase family. The amidinotransferase family comprises glycine (EC:2.1.4.1) and inosamine (EC:2.1.4.2) amidinotransferases, enzymes involved in creatine and streptomycin biosynthesis respectively. This family also includes arginine deiminases, EC:3.5.3.6. These enzymes catalyse the reaction: arginine+H2O<=>citruline+NH3. Also found in this family is the *Streptococcus* anti tumour glycoprotein. Enzymes or proteins with an L-arginie:glycine-amidinotransferase (AGAT) activity are also described to possess a conserved domain that belongs to the PFAM Family: Amidinotransf (PF02274) (Marchler-Bauer A et al. (2017), "CDD/SPARCLE: functional classification of proteins via subfamily domain architectures.", Nucleic Acids Res. 45(D1):D200-D203.) as described also in the following publications: Pissowotzki K et al., Mol Gen Genet 1991; 231:113-123 (PUBMED:1881369 EPMC:1881369); D'Hooghe I et al., J Bacteriol 1997; 179:7403-7409 (PUBMED:9393705 EPMC:9393705); Kanaoka M et al., Jpn J Cancer Res 1987; 78:1409-1414 (PUBMED:3123442 EPMC:3123442).

In the microorganism of the present invention the gene coding for a protein having the function of an L-arginine:glycine amidinotransferase may further be overexpressed. Overexpression of a gene is generally achieved by increasing the copy number of the gene and/or by functionally linking the gene with a strong promoter and/or by enhancing the ribosomal binding site and/or by codon usage optimization of the start codon or of the whole gene or a combination comprising a selection or all methods mentioned above.

The protein having the function of an L-arginine:glycine amidiotransferase in the microorganism of the present invention may comprise an amino acid sequence which is at least 80% homologous, preferably at least 90% homologous to the amino acid sequence according to SEQ ID NO:11. In a further embodiment of the present invention the amino acid sequence of the L-arginine:glycine amidinotransferase is identical to amino acid sequence according to SEQ ID NO:11.

In a particular embodiment of the present invention, the protein having the enzymic activity of a glyoxylate aminotransferase in the microorganism according to the present invention comprises an amino acid sequence which is at least 80% homologous to the amino acid sequence according to SEQ ID NO: 2, according to SEQ ID NO: 5 or according to SEQ ID NO: 8.

The microorganism of the present invention may belong to the genus *Corynebacterium*, preferably *Corynebacterium glutamicum* (*C. glutamicum*), or to the genus Enterobacteriaceae, preferably *Escherichia coli* (*E. coli*), or to the genus *Pseudomonas*, preferably *Pseudomonas putida* (*P. putida*).

An increased enzymic activity of a protein in a microorganism, in particular in the microorganism of the present invention compared to the respective activity in the wildtype microorganism, can be achieved for example by a mutation of the protein, in particular by a mutation conferring the protein a feedback resistance e.g. against a product of an enzyme-catalyzed reaction, or by increased expression of a gene encoding the protein having the enzymic activity compared to the expression of the respective gene in the wildtype microorganism.

Increased expression or overexpression of a gene in a microorganism, in particular in the microorganism of the present invention compared to the respective activity in the wildtype microorganism, can be achieved by increasing the copy number of the gene and/or by an enhancement of regulatory factors, e.g. by functionally linking the gene with a strong promoter and/or by enhancing the ribosomal binding site and/or by codon usage optimization of the start codon or of the whole gene. The enhancement of such regulatory factors which positively influence gene expression can, for example, be achieved by modifying the promoter sequence upstream of the structural gene in order to increase the effectiveness of the promoter or by completely replacing said promoter with a more effective or a so-called strong promoter. Promoters are located upstream of the gene. A promoter is a DNA sequence consisting of about 40 to 50 base pairs and which constitutes the binding site for an RNA polymerase holoenzyme and the transcriptional start point, whereby the strength of expression of the controlled polynucleotide or gene can be influenced. Generally, it Is possible to achieve an overexpression or an increase in the expression of genes in bacteria by selecting strong promoters, for example by replacing the original promoter with strong, native (originally assigned to other genes) promoters or by modifying certain regions of a given, native promoter (for example its so-called −10 and −35 regions) towards a consensus sequence, e.g. as taught by M. Patek et al. (Microbial Biotechnology 6 (2013), 103-117) for *C. glutamicum*. An example for a "strong" promoter is the superoxide dismutase (sod) promoter ("Psod"; Z. Wang et al., Eng. Life Sci. 2015, 15, 73-82). A "functional linkage" Is understood to mean the sequential arrangement of a promoter with a gene, which leads to a transcription of the gene.

The genetic code is degenerated which means that a certain amino acid may be encoded by a number of different triplets. The term codon usage refers to the observation that a certain organism will typically not use every possible codon for a certain amino acid with the same frequency. Instead an organism will typically show certain preferences for specific codons meaning that these codons are found more frequently in the coding sequence of transcribed genes of an organism. If a certain gene foreign to its future host, i.e. from a different species, should be expressed in the future host organism the coding sequence of said gene should then be adjusted to the codon usage of said future host organism (i.e. codon usage optimization).

The above-mentioned problem is further solved by a method for the fermentative production of guanidino acetic acid (GAA), comprising the steps of a) cultivating the microorganism according to the present invention as defined above in a suitable medium under suitable conditions, and b) accumulating GAA in the medium to form an GAA containing fermentation broth.

The method of the present invention may further comprise the step of isolating GAA from the fermentation broth.

The method according to the present invention may further comprise the step of drying and/or granulating the GAA containing fermentation broth.

The present invention further concerns a microorganism as defined above, further comprising a gene coding for an enzyme having the activity of a guanidinoacetate N-methyltransferase (EC: 2.1.1.2). Preferably, the gene coding for an enzyme having the activity of a guanidinoacetate N-methyltransferase is overexpressed.

The present invention also concerns a method for the fermentative production of creatine, comprising the steps of a) cultivating the microorganism according to the present invention comprising a gene coding for an enzyme having the activity of a guanidinoacetate N-methyltransferase in a suitable medium under suitable conditions, and b) accumulating creatine in the medium to form a creatine containing fermentation broth.

Preferably, the method further comprises isolating creatine from the creatine containing fermentation broth. creatine may be extracted from fermentation broth by isoelectric point method and/or ion exchange method. Alternatively, creatine can be further purified by a method of recrystallization in water.

Experimental Section

A) Materials and Methods

Chemicals

Kanamycin solution from *Streptomyces kanamyceticus* was purchased from Sigma Aldrich (St. Louis, USA, Cat. no. K0254). IPTG (Isopropyl β-D-1-thiogalactopyranoside) was purchased from Carl-Roth (Karlsruhe, Germany, Cat. no. 2316.4.). If not stated otherwise, all other chemicals were purchased analytically pure from Merck (Darmstadt, Germany), Sigma Aldrich (St. Louis, USA) or Carl-Roth (Karlsruhe, Germany).

Cultivation for Cell Proliferation

If not stated otherwise, cultivation/incubation procedures were performed as follows herewith:

a. LB broth (MILLER) from Merck (Darmstadt, Germany; Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 30° C. and 200 rpm.

b. LB agar (MILLER) from Merck (Darmstadt, Germany, Cat. no. 110283) was used for cultivation of *E. coli* strains on agar plates. The agar plates were incubated at 30° C. in an INCU-Line® mini incubator from VWR (Radnor, USA).

c. Brain heart infusion broth (BHI) from Merck (Darmstadt, Germany, Cat. no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors GmbH (Bottmingen, Switzerland) at 30° C. and 200 rpm.

d. Brain heart agar (BHI-agar) from Merck (Darmstadt, Germany, Cat. no. 113825) was used for cultivation of *C. glutamicum* strains on agar plates. The agar plates were incubated at 30° C. in an incubator from Heraeus Instruments with Kelvitron® temperature controller (Hanau, Germany).

e. For cultivating *C. glutamicum* after electroporation, BHI-agar (Merck, Darmstadt, Germany, Cat. no. 113825) was supplemented with 134 g/l sorbitol (Carl Roth GmbH+Co. KG, Karlsruhe, Germany), 2.5 g/l yeast extract (Oxoid/ThermoFisher Scientific, Waltham, USA, Cat. no. LP0021) and 25 mg/l kanamycin. The agar plates were incubated at 30° C. in an incubator from Heraeus Instruments with Kelvitron® temperature controller (Hanau, Germany).

Determining Optical Density of Bacterial Suspensions a. The optical density of bacterial suspensions in shake flask cultures was determined at 600 nm (OD600) using the BioPhotometer from Eppendorf AG (Hamburg, Germany).

b. The optical density of bacterial suspensions produced in the Wouter Duetz (WDS) micro fermentation system (24-Well Plates) was determined at 680 nm (OD680) with the GENios™ plate reader from Tecan Group AG (Männedorf, Switzerland).

Centrifugation a. Bacterial suspensions with a maximum volume of 2 ml were centrifuged in 1.5 ml or 2 ml reaction tubes (e.g. Eppendorf Tubes® 3810X) using an Eppendorf 5417 R benchtop centrifuge (5 min. at 13,000 rpm).

b. Bacterial suspensions with a maximum volume of 50 ml were centrifuged in 15 ml or 50 ml centrifuge tubes (e.g. Falcon™ 50 ml Conical Centrifuge Tubes) using an Eppendorf 5810 R benchtop centrifuge for 10 min. at 4,000 rpm.

DNA Isolation

Plasmid DNA was isolated from *E. coli* cells using the QIAprep Spin Miniprep Kit from Qiagen (Hilden, Germany, Cat. No. 27106) according to the instructions of the manufacturer.

Polymerase Chain Reaction (PCR)

PCR with a proof reading (high fidelity) polymerase was used to amplify a desired segment of DNA for Sanger sequencing or DNA assembly. Non-proof-reading polymerase Kits were used for determining the presence or absence of a desired DNA fragment directly from *E. coli* or *C. glutamicum* colonies.

a. The Phusion® High-Fidelity DNA Polymerase Kit (Phusion Kit) from New England BioLabs Inc. (Ipswich, USA, Cat. No. M0530) was used for template-correct amplification of selected DNA regions according to the instructions of the manufacturer (see Table 2).

TABLE 2

Thermocycling conditions for PCR with Phusion ® High-Fidelity DNA Polymerase Kit from New England BioLabs Inc.
PCR Program

| Step | Time [min.:sec.] | T [° C.] | Description |
|---|---|---|---|
| 1 | 00:30 | 98 | Initial denaturation step |
| 2 | 00:05 | 98 | Denaturation step |
| 3 | 00:30 | 60 | Annealing step |
| 4 | 00:xx | 72 | Elongation step 1 min. per kb DNA Repeat step 2 to 4:35× |
| 5 | 05:00 | 72 | Final elongation step |
| 6 | Hold | 4 | Cooling step | b. Taq PCR Core Kit (Taq Kit) from Qiagen (Hilden, Germany, Cat. No. 201203) was used to amplify a desired segment of DNA in order to confirm its presence. The kit was used according to the instructions of the manufacturer (see Table 3).

TABLE 3

Thermocycling conditions for PCR with Taq PCR Core Kit (Taq Kit) from Qiagen.
PCR Program

| Step | Time [min.:sec.] | T [° C.] | Description |
|---|---|---|---|
| 1 | 05:00 | 94 | Initial denaturation step |
| 2 | 00:30 | 94 | Denaturation step |
| 3 | 00:30 | 52 | Annealing step |
| 4 | 01:20 | 72 | Elongation step 1 min. per kb DNA Repeat step 2 to 4:35× |

TABLE 3-continued

Thermocycling conditions for PCR with
Taq PCR Core Kit (Taq Kit) from Qiagen.
PCR Program

| Step | Time [min.:sec.] | T [° C.] | Description |
|---|---|---|---|
| 5 | 04:00 | 72 | Final elongation step |
| 6 | Hold | 4 | Cooling step | c. SapphireAmp® Fast PCR Master Mix (Sapphire Mix) from Takara Bio Inc (Takara Bio Europe S.A.S., Saint-Germain-en-Laye, France, Cat. No. RR350A/B) was used as an alternative to confirm the presence of a desired segment of DNA in cells taken from *E. coli* or *C. glutamicum* colonies according to the instructions of the manufacturer (see Table 4).

TABLE 4

Thermocycling conditions for PCR with SapphireAmp ®
Fast PCR Master Mix (Sapphire Mix) from Takara Bio Inc.
PCR Program

| Step | Time [min.:sec.] | T [° C.] | Description |
|---|---|---|---|
| 1 | 01:00 | 94 | Initial denaturation step |
| 2 | 00:05 | 98 | Denaturation step |
| 3 | 00:05 | 55 | Annealing step |
| 4 | 00:05 | 72 | Elongation step Repeat step 2 to 4:30× |
| 5 | 04:00 | 72 | Final elongation step |
| 6 | Hold | 4 | Cooling step | d. All oligonucleotide primers were synthesized by Eurofins Genomics GmbH (Ebersberg, Germany) using the phosphoramidite method described by McBride and Caruthers (1953).

e. As PCR template either a suitably diluted solution of isolated plasmid DNA or of total DNA isolated from a liquid culture or the total DNA contained in a bacterial colony (colony PCR) was used. For said colony PCR the template was prepared by taking cell material with a toothpick from a colony on an agar plate and placing the cell material directly into the PCR reaction tube. The cell material was heated for 10 sec. with 800 W in a microwave oven type Mikrowave & Grill from SEVERIN Elektrogeräte GmbH (Sundern, Germany) and then the PCR reagents were added to the template in the PCR reaction tube.

f. All PCR reactions were carried out in PCR cyclers type Mastercycler or Mastercycler nexus gradient from Eppendorf AG (Hamburg, Germany).

Restriction Enzyme Digestion of DNA

For restriction enzyme digestions either "FastDigest restriction endonucleases (FD)" (ThermoFisher Scientific, Waltham, USA) or restriction endonucleases from New England BioLabs Inc. (Ipswich, USA) were used. The reactions were carried out according to the instructions of the manufacturer's manual.

Determining the Sizes of DNA Fragments a. The sizes of small DNA fragments (<1000 bps) were usually determined by automatic capillary electrophoresis using the QIAxcel from Qiagen (Hilden, Germany).

b. If DNA fragments needed to be isolated or If the DNA fragments were >1000 bps DNA was separated by TAE agarose gel electrophoresis and stained with GelRed® Nucleic Acid Gel Stain (Biotium, Inc., Fremont, Canada). Stained DNA was visualized at 302 nm.

Purification of PCR Amplificates and Restriction Fragments

PCR amplificates and restriction fragments were cleaned up using the QIAquick PCR Purification Kit from Qiagen (Hilden, Germany; Cat. No. 28106), according to the manufacturer's instructions. DNA was eluted with 30 µl 10 mM Tris*HCl (pH 8.5).

Determining DNA Concentration

DNA concentration was measured using the NanoDrop Spectrophotometer ND-1000 from PEQLAB Biotechnologie GmbH, since 2015 VWR brand (Erlangen, Germany).

Assembly Cloning

Plasmid vectors were assembled using the "NEBuilder HiFi DNA Assembly Cloning Kit" purchased from New England BioLabs Inc. (Ipswich, USA, Cat. No. E5520). The reaction mix, containing the linear vector and at least one DNA insert, was incubated at 50° C. for 60 min. 0.5 µl of Assembly mixture was used for each transformation experiment.

Chemical Transformation of *E. coli*

For plasmid cloning, chemically competent "NEB® Stable Competent *E. coli* (High Efficiency)" (New England BioLabs Inc., Ipswich, USA, Cat. No. C3040) were transformed according to the manufacturers protocol. Successfully transformed cells were selected on LB agar supplemented with 25 mg/A kanamycin.

Transformation of *C. glutamicum*

Transformation of *C. glutamicum* with plasmid-DNA was conducted via electroporation using a "Gene Pulser Xcell" (Bio-Rad Laboratories GmbH, Feldkirchen, Germany) as described by Ruan et al. (2015). Electroporation was performed in 1 mm electroporation cuvettes (Bio-Rad Laboratories GmbH, Feldkirchen, Germany) at 1.8 kV and a fixed time constant set to 5 ms. Transformed cells were selected on BHI-agar containing 134 g/l sorbitol, 2.5 g/l Yeast Extract and 25 mg/l kanamycin.

Determining Nucleotide Sequences

Nucleotide sequences of DNA molecules were determined by Eurofins Genomics GmbH (Ebersberg, Germany) by cycle sequencing, using the dideoxy chain termination method of Sanger et al. (Proceedings of the National Academy of Sciences USA 74, 5483-5487, 1977). Clonemanager Professional 9 software from Scientific & Educational Software (Denver, USA) was used to visualise and evaluate the sequences.

Glycerol Stocks of *E. coli* and *C. glutamicum* Strains

For long time storage of *E. coli* and *C. glutamicum* strains glycerol stocks were prepared. Selected *E. coli* clones were cultivated in 10 ml LB medium supplemented with 2 g/l glucose. Selected *C. glutamicum* clones were cultivated in 10 ml twofold concentrated BHI medium supplemented with 2 g/l glucose. Media for growing plasmid containing *E. coli* and *C. glutamicum* strains were supplemented with 25 mg/l kanamycin. The medium was contained in 100 ml Erlenmeyer flasks with 3 baffles. It was inoculated with a loop of cells taken from a colony. The culture was then incubated for 18 h at 30° C. and 200 rpm. After said incubation period 1.2 ml 85% (v/v) sterile glycerol were added to the culture. The obtained glycerol containing cell suspension was then aliquoted in 2 ml portions and stored at −80° C.

GAA Production in Millilitre-Scale Cultivations

The millilitre-scale cultivation system according to Duetz (2007) was used to assess the GAA-production of the strains. For this purpose, 24-deepwell microplates (24 well WDS plates) from EnzyScreen BV (Heemstede, Netherlands, Cat. no. CR1424) filled with 2.5 ml medium per well were used.

Precultures of the strains were done in 10 ml seed medium (SM). The medium was contained in a 100 ml Erlenmeyer flask with 3 baffles. It was inoculated with 100 µl of a glycerol stock culture and the culture was incubated for 24 h at 30° C. and 200 rpm. The composition of the seed medium (SM) is shown in Table 5.

TABLE 5

Seed medium (SM)

| Components | Concentration (g/l) |
|---|---|
| Yeast extract FM902 (Angel Yeast Co., LTD, Hubei, P.R. China) | 10 |
| Urea | 1.5 |
| $KH_2PO_4$ | 0.5 |
| $K_2HPO_2$ | 0.5 |
| $MgSO_4 * 7 H_2O$ | 1 |
| Biotin | 0.0001 |
| Thiamine hydrochloride | 0.0001 |
| $FeSO_4 * 7 H_2O$ | 0.01 |
| $MnSO_4 * H_2O$ | 0.01 |
| Glucose | 20 |
| Kanamycin | 0.025 |
| pH = 7.0 | |

After said incubation period the optical densities OO600 of the precultures were determined. The volume, needed to inoculate 2.5 ml of production medium (PM) to an OO600 of 0.1, was sampled from the preculture, centrifuged (1 min at 5000 g) and the supernatant was discarded. Cells were 3 then resuspended in 100 µl of production medium.

The main cultures were started by inoculating the 2.4 ml production medium (PM) containing wells of the 24 Well WDS-Plate with each 100 µl of the resuspended cell from the precultures. The composition of the production medium (PM) is shown in Table 6.

TABLE 6

Production medium (PM)

| Components | Concentration (g/l) |
|---|---|
| 3-(N-morpholino)propanesulfonic acid (MOPS) | 40 |
| Yeast extract FM902 (Angel Yeast Co., LTD, Hubei, P.R. China) | 1.5 |
| $(NH_4)_2SO_4$ | 10 |
| $NH_4Cl$ | 15 |
| Trisodium citrate * 2 $H_2O$ | 10 |
| Urea | 1 |
| $KH_2PO_4$ | 0.5 |
| $K_2HPO_4$ | 0.5 |
| Ammonium acetate | 7.7 |
| $MgSO_4 * 7 H_2O$ | 1 |
| Biotin | 0.0001 |
| Thiamine hydrochloride | 0.0001 |
| $FeSO_4 * 7 H_2O$ | 0.01 |

TABLE 6-continued

Production medium (PM)

| Components | Concentration (g/l) |
|---|---|
| $MnSO_4 * H_2O$ | 0.01 |
| $ZnSO_4 * 7 H_2O$ | 0.000015 |
| $CuSO_4 * 5 H_2O$ | 0.0004 |
| Antifoam XFO-1501 (Ivanhoe Industries Inc., Zion, USA) | 0.5 |
| Glucose | 40 |
| IPTG (Isopropyl β-D-1-thiogalactopyranoside) | 1 mM |
| Kanamycin | 0.025 |
| pH = 7.2 | |

The main cultures were incubated for 72 h at 30° C. and 300 rpm in an Infors HT Multitron standard incubator shaker from Infors GmbH (Bottmingen, Switzerland) until complete consumption of glucose. The glucose concentration in the suspension was analysed with the blood glucose-meter OneTouch Vital® from LifeScan (Johnson & Johnson Medical GmbH, Neuss, Germany).

After cultivation the culture suspensions were transferred to a deep well microplate. A part of the culture suspension was suitably diluted to measure the OD660. Another part of the culture was centrifuged and the concentration of GAA in the supernatant was analyzed as described below.

Determination of L-arginine and Glycine Content in Yeast Pepton FM902

As yeast extract FM902 (Angel Yeast Co., LTD, Hubei, P.R.China) contains various peptides and amino acids, its content of L-arginine and glycine was measured as follows.

For measuring free amino acids, the samples were prepared by dissolving 1 g of yeast extract in 20 ml of water. The solution was fled up with water to a total volume of 25 ml, mixed thoroughly and filtered using a 0.2 µM nylon syringe filter.

For measuring total amino acids (free amino acids plus amino acids bound in peptides), the samples were prepared by dissolving 1 g yeast extract in 10 ml 6M HCl and incubating them for 24 h at 110° C. Then, water was added up to a total volume of 25 ml. The solution was mixed thoroughly and filtered using a 0.2 µM nylon syringe filter.

The concentrations of L-arginine and glycine in the samples were determined by ion exchange chromatography using a SYKAM S433 amino acid analyzer from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aqueous solution containing in 20 l 263 g trisodium citrate, 120 g citric acid, 1100 ml methanol, 100 ml 37% HCl and 2 ml octanoic acid (final pH 3.5) was used. As buffer B an aqueous solution containing in 20 l 392 g trisodium citrate, 100 g boric acid and 2 ml octanoic acid (final pH 10.2) was used. The free amino acids were coloured with ninhydrin through post-column derivatization and detected photometrically at 570 nm.

Table 7 shows the content of free and total L-arginine and glycine determined in yeast extract FM902 (Angel Yeast Co., LTD, Hubei, P.R.China), as well as the resulting amounts in the production medium (PM).

TABLE 7

Content of L-arginine and glycine in yeast extract (YE) FM902 and resulting concentrations in production medium (PM) containing 1.5 g/l YE.

| Amino acid | Free amino acid in YE | Total amino acid in YE | Resulting free amino acid in PM | Resulting total amino acid in PM |
|---|---|---|---|---|
| L-arginine | 15.1 g/kg | 32.1 g/kg | 22.7 mg/l | 48.2 mg/l |
| glycine | 6.9 g/kg | 30.5 g/kg | 10.4 mg/l | 45.7 mg/l |

Quantification of GAA

Samples were analyzed with an analyzing system from Agilent, consisting of a HPLC "Infinity 1280" coupled with a mass analyzer "Triple Quad 6420" (Agilent Technologies Inc., Santa Clara, USA). Chromatographic separation was done on the Atlantis HILIC Silica column, 4.8×250 mm, 5 μm (Waters Corporation, Milford, USA) at 35° C. Mobile phase A was water with 10 mM ammonium formate and 0.2% formic acid. Mobile phase B was a mixture of 90% acetonitrile and 10% water, 10 mM ammonium formate were added to the mixture. The HPLC system was started with 100% B, followed by a linear gradient for 22 min and a constant flow rate of 0.8 mL/min to 66% B. The mass analyzer was operated in the ESI positive ionization mode. For detection of GAA the m/z values were monitored by using an MRM fragmentation [M+H]+ 118-76. The limit of quantification (LOQ) for GAA was fixed to 7 ppm.

B) Experimental Results

Example 1: Cloning of the Gene GGT1 Coding for a Glyoxylate Aminotransferase from *Arabidopsis thaliana*

The gene GGT1 of *Arabidopsis thaliana* (Genbank accession Number NM_102180, SEQ ID NO:1) codes for a glutamate:glyoxylate aminotransferase (Genbank accession Number NP_584192, SEQ ID NO:2). The protein has been shown to catalyze the reactions glyoxylate+L-alanine=glycine+pyruvate (EC 2.6.1.44), 2-oxoglutarate+L-alanine=L-glutamate+pyruvate (EC 2.6.1.2), and 2-oxoglutarate+glycine=glyoxylate+L-glutamate (EC 2.6.1.4; Liepman A H, Olsen U., Plant Physiol. 2003 January; 131(1):215-27. doi: 10.1104/pp. 011480).

Using the software tool "Codon Optimization Tool" (integrated DNA Technologies Inc., Coralville, Iowa, USA) the amino acid sequence of the GGT1 protein was translated back into a DNA sequence optimized for the codon usage of *C. glutamicum*. A Shine-Dalgarno-Sequenz was added directly upstream of the open reading frame (AGGAAAGGAGAGGATTG; Shi F, Luan M, Li Y, AMB Express. 2018 Apr. 18; 8(1):61. doi: 10.1188/s13588-018-0595-2) (SEQ ID NO: 23) and the ends of the resulting sequence were expanded with motifs for subsequent subcloning. The resulting DNA sequence AtGGT1_opt_RBS (SEQ ID NO:3) was ordered for gene synthesis from Eurofins Genomics GmbH (Ebersberg, Germany) and K was delivered as part of a cloning plasmid conferring resistance to ampicillin (designated as pEX-A258-AtGGT1_opt_RBS).

Example 2: Cloning of the Gene GGT2 Coding for a Glyoxylate Aminotransferase from *Arabidopsis thaliana*

The gene AOAT2 (synonym: GGT2) of *Arabidopsis thaliana* (Genbank accession Number NM_001038185, SEQ ID NO:4) codes for alanine-2-oxoglutarate aminotransferase 2 (Genbank accession Number NP_001031282, SEQ ID NO:5). The protein has been shown to catalyze the reactions glyoxylate+L-alanine=glycine+pyruvate (EC 2.6.1.44), 2-oxoglutarate+L-alanine=L-glutamate+pyruvate (EC 2.6.1.2), and 2-oxoglutarate+glycine=glyoxylate+L-glutamate (EC 2.6.1.4; Liepman A H, Olsen U. (2003), Plant Physiol. 2003 January; 131(1):215-27. doi: 10.1104/pp.011480).

Using the software tool "Codon Optimization Tool" (integrated DNA Technologies Inc., Coralville, Iowa, USA) the amino acid sequence of the GGT2 protein was translated back into a DNA sequence optimized for the codon usage of *C. glutamicum*. A Shine-Dalgarno-Sequenz was added directly upstream of the open reading frame (AGGAAAGGAGAGGATTG; Shi, 2018) (SEQ ID NO: 23) and the ends of the resulting sequence were expanded with motifs for subsequent subcloning.

The resulting DNA sequence AtGGT2_opt_RBS (SEQ ID NO:8) was ordered for gene synthesis from Eurofins Genomics GmbH (Ebersberg, Germany) and K was delivered as part of a cloning plasmid conferring resistance to ampicillin (designated as pEX-A258-AtGGT2_opt_RBS).

Example 3: Cloning of the Gene agt Coding for a Glyoxylate Aminotransferase from *Thermococcus litoralis*

The gene agt of *Thermococcus litoralis* (Genbank accession Number AB033998, SEQ ID NO:7) codes for an alanine:glyoxylate aminotransferase (Genbank accession Number BAB40321, SEQ ID NO:8). The protein has been shown to catalyze the reactions glyoxylate+L-alanine=glycine+pyruvate (EC 2.6.1.44) and glyoxylate+L-serine=glycine+3-hydroxypyruvate (EC 2.6.1.45; Sakuraba, H. et al., J Bacteriol. 2004 August; 186(16): 5513-5518. doi: 10.1128/JB.188.18.5513-55182004).

Using the software tool "Codon Optimization Tool" (Integrated DNA Technologies Inc., Coralville, Iowa, USA) the amino acid sequence of the Agt protein was translated back into a DNA sequence optimized for the codon usage of *C. glutamicum*. A Shine-Dalgarno-Sequenz was added directly upstream of the open reading frame (AGGAAAGGAGAGGATTG; Shi F, Luan M, LI Y, AMB Express. 2018 Apr. 18; 8(1)-81. doi: 10.1188/s13568-018-0595-2) (SEQ ID NO: 23) and the ends of the resulting sequence were expanded with motifs for subsequent subcloning. The resulting DNA sequence (SEQ ID NO:9) was ordered for gene synthesis from Eurofins Genomics GmbH (Ebersberg, Germany) and K was delivered as part of a cloning plasmid conferring resistance to ampicillin (designated as pEX-A258-AGT_TI_op_RBS).

Example 4: Cloning of the Gene AGAT_Mp Coding for an L-Arginin:Glycine Amidinotransferase (AGAT, EC 2.1.4.1) from *Moorea producens*

*Moorea producens* is a filamentous cyanobacterium. The genome of the *Moorea producens* strain PAL-8-15-08-1 was published by Leao et al. (Leao T, Castelão G, Korobeynikov A, Monroe E A, Podel S, Glukhov E, Alen E E, Gerwick W H, Gerwick L, Proc Natl Acad Sci USA. 2017 Mar. 21; 114(12):3198-3203. doi: 10.1073/pnas.1618558114; Genbank accession Number CP017599.1). It contains an open reading frame putatively coding for a L-arginine:glycine amidinotransferase (AGAT, EC 2.1.4.1; locus_tag BJP34_00300 shown in SEQ ID NO:10). SEQ ID NO:11 shows the derived amino acid sequence (Genbank accession Number WP_070390802).

Using the software tool "GeneOptimizer" (Geneart/ThermoFisher Scientific, Waltham, USA) this amino acid sequence was translated back into a DNA sequence optimized for the codon usage of *C. glutamicum*. Its ends were expanded with sequences for assembly cloning and 5 base pairs upstream of the open reading frame a Shine-Dalgarno-Sequenz (AGGA) was added. The resulting DNA sequence (SEQ ID NO:12) was ordered for gene synthesis from Invitrogen/Geneart (Thermo Fisher Scientific, Waltham, USA) and it was delivered as part of a cloning plasmid (designated as pMA-T_AGAT_Mp).

Example 5: Cloning of AGAT_Mp into the Expression Plasmid pEC-XK99E

The *E. coli-C. glutamicum* shuttle plasmid pEC-XK99E (Genbank accession Number AY219882) was digested using the restriction endonuclease SmaI. Terminal phosphates were removed using the "FastAP Thermosensitive Alkaline Phosphatase" (Thermo Fisher Scientific, Waltham, USA). The DNA was then purified with the "QIAquick PCR Purification Kit" (Qiagen GmbH, Hilden, Germany).

The cloning plasmid pMA-T_AGAT_Mp was digested with MluI+AatII and the resulting fragments were blunted using the "Fast DNA End Repair Kit" (Thermo Fisher Scientific, Waltham, USA). They were separated by agarose gel electrophoresis (0.8% agarose in TAE buffer) and the band corresponding to "AGAT_Mp" (1174 bp) was cut out. Its DNA was purified using the "QIAquick Gel Extraction Kit" (Qiagen GmbH, Hilden, Germany).

The AGAT_Mp fragment and the linearized pEC-XK99E were ligated using the "Ready-To-Go T4 DNA ligase" (GE Healthcare Europe GmbH, Freiburg, Germany). The ligation product was transformed into "NEB Stable Competent *E. coli* (High Efficiency)" (New England Biolabs, Ipswich, USA) and the cells were grown on LB agar containing 25 mg/A kanamycin. Appropriate clones were identified by restriction enzyme digestion and DNA sequencing. The resulting plasmid was named pEC-XK99E_AGAT_Mp.

Example 6: Cloning of the Glyoxylate Aminotransferase Genes into the Expression Plasmid pEC-XK99E_AGAT_Mp The Plasmid pEC-XK99E_AGAT_Mp was digested using the restriction endonuclease BamHI and terminal phosphates were removed using the "FastAP Thermosensitive Alkaline Phosphatase" (Thermo Fisher Scientific, Waltham, USA). The digested DNA was then purified using the "QIAquick Gel Extraction Kit" (Qiagen GmbH, Hilden, Germany).

The cloning plasmids pEX-A258-AtGGT1_opt_RBS, pEX-A258-AtGGT2_opt_RBS and pEX-A258-AGT_TI_opt_RBS were each digested with BamHI and BsaI. The cut plasmids were purified using the "QIAquick PCR Purification Kit" (Qiagen GmbH, Hilden, Germany).

The digested pEC-XK99E_AGAT_Mp was ligated with each of the digested cloning plasmids using the "Ready-To-Go T4 DNA ligase" (GE Healthcare Europe GmbH, Freiburg, Germany). The ligation products were transformed into "NEB Stable Competent *E. coli* (High Efficiency)" (New England Biolabs, Ipswich, USA) and the cells were grown on LB agar containing 25 mg/l kanamycin. Appropriate clones were identified by restriction enzyme digestion and DNA sequencing. The resulting plasmids are shown in Table 8. They provide the AGAT_Mp gene and a respective glyoxylate aminotransferase in an operon like structure under control of the strong IPTG inducible trc-promoter.

TABLE 8

*E. coli-C. glutamicum* shuttle plasmids used for gene expression.

| Plasmid | Note |
| --- | --- |
| pEC-XK99E | Empty *E. coli - C. glutamicum* shuttle plasmid (Genbank accession Number AY219682) |
| pEC-XK99E_AGAT_Mp | Expression of AGAT_Mp (*Moorea producens*); |
| pEC-XK99E_AGAT_Mp_AtGGT1 | Expression of AGAT_Mp and GGT1, coding for glutamate:glyoxylate aminotransferase of *Arabidopsis thaliana* (Genbank accession Number NP_564192) |
| pEC-XK99E_AGAT_Mp_AtGGT2 | Expression of AGAT_Mp and GGT2, coding for alanine-2-oxoglutarate aminotransferase 2 of *Arabidopsis thaliana* (Genbank accession Number NP_001031262) |
| pEC-XK99E_AGAT_Mp_AGT_TI | Expression of AGAT_Mp and AGT_TI, coding for glutamate:glyoxylate aminotransferase of *Thermococcus litoralis* (Genbank accession Number BAB40321) |

Example 7: Chromosomal Insertion of the Sod Promoter Upstream of the carAB Operon in ATCC13032

To Improve the production of L-arginine, the strong sod-promoter was inserted Into the genome of ATCC13032 upstream of the carAB operon. Therefore, the plasmid pK18mobsacB_Psod-carAB was constructed as follows. pK18mobsacB (Schäfer, A. et al., Gene. 1994 Jul. 22; 145(1):69-73. doi: 10.1016/0378-1119(94)90324-7) was cut using EcoRI+HindIII and the linearized vector DNA (5870 bps) was cut out of an agarose gel. The DNA was extracted using the "QIAquick PCR Purification Kit" (Qiagen GmbH, Hilden, Germany).

For constructing the insert, three DNA fragments were created by PCR with the following pairs of primers (genomic DNA of ATCC13032 as template):
PsodcarAB-LA-F (SEQ ID NO:13)+PsodcarAB-LA-R (SEQ ID NO:14)
=left homology arm (1025 bps)
PsodcarAB-F (SEQ ID NO:15)+PsodcarAB-R (SEQ ID NO:18)
=sod-promoter (250 bps)
PsodcarAB-RA-F SEQ ID NO:17)+PsodcarAB-RA-R (SEQ ID NO:18)
=right homology arm (944 bps)

The product DNAs were purified using the "QIAquick PCR Purification Kit" (Qiagen GmbH, Hilden, Germany). The linearized plasmid and the PCR products were then assembled using the "NEBuilder HiFi DNA Assembly Cloning Kit" (New England BioLabs Inc., Ipswich, USA, Cat. No. E5520). Proper plasmid clones were identified by restriction digestion and DNA sequencing.

The resulting plasmid pK18mobsacB_Psod-carAB was then transformed into ATCC13032 by electroporation. Chromosomal integration (resulting from a first recombination event) was selected by plating on BHI agar supplemented with 134 g/l sorbitol, 2.5 g/l yeast extract and 25 mg/A kanamycin. The agar plates were incubated for 48 h at 33° C.

Individual colonies were transferred onto fresh agar plates (with 25 mg/A kanamycin) and incubated for 24 h at 33° C. Liquid cultures of these clones were cultivated for 24 h at 33° C. in 10 ml BHI medium contained in 100 ml Erlenmeyer flasks with 3 baffles. To isolate clones that have encountered a second recombination event, an aliquot was taken from each liquid culture, suitably diluted and plated (typically 100 to 200 µl) on BHI agar supplemented with 10% saccharose. These agar plates were incubated for 48 h at 33° C. The colonies growing on the saccharose containing agar plates were then examined for kanamycin sensitivity. To do so a toothpick was used to remove cell material from the colony and to transfer it onto BHI agar containing 25 mg/l kanamycin and onto BHI agar containing 10% saccharose. The agar plates were incubated for 80 h at 33° C. Clones that proved to be sensitive to kanamycin and resistant to saccharose were examined by PCR and DNA sequencing for the appropriate integration of the sod promoter. The resulting strain was named ATCC13032_Psod-carAB.

Example 6: Chromosomal Deletion of the Gene aceB (NCgl2247) in *C. glutamicum* ATCC13032_Psod-carAB To reduce the metabolic flux of glyoxylate to L-malate, the gene aceB (NCgl2247), coding for malate synthase (EC 2.3.3.9), was to be deleted in strain ATCC13032_Psod-carAB.

Therefore, the plasmid pK18mobsacB_DaceB was constructed as follows. Plasmid pK18mobsacB (Schäfer, 1994) was cut using XbaI and the linearized vector DNA (5721 bps) was purified using the "QIAquick Gel Extraction Kit" (Qiagen GmbH, Hilden, Germany).

For constructing the insert, two DNA fragments were created by PCR with the following pairs of primers (genomic DNA of ATCC13032 as template):
1f-aceB-D2_vec (SEQ ID NO:19)+1r-aceB-D2_aceB (SEQ ID N020)
=left homology arm (1065 bps)
2f-aceB-D2_aceB (SEQ ID NO:21)+2r-aceB-D2_Vec (SEQ ID NO:22)
=left homology arm (1080 bps)

The product DNAs were purified using the "QIAquick PCR Purification Kit" (Qiagen GmbH, Hilden, Germany). The linearized plasmid and the PCR products were then assembled using the "NEBuilder HiFi DNA Assembly Cloning Kit" (New England BioLabs Inc., Ipswich, USA, Cat. No. E5520). The resulting deletion vector was named pK18mobsacB_DaceB. It was verified by restriction enzyme digestion and DNA sequencing.

For deleting the aceB gene, pK18mobsacB_DaceB was transformed into ATCC13032_Psod-carAB by electroporation. Chromosomal integration (resulting from a first recombination event) was selected by plating on BHI agar supplemented with 134 g/l sorbitol, 2.5 g/l yeast extract and 25 mg/A kanamycin. The agar plates were incubated for 48 h at 33° C.

Individual colonies were transferred onto fresh agar plates (with 25 mg/l kanamycin) and incubated for 24 h at 33° C. Liquid cultures of these clones were cultivated for 24 h at 33° C. in 10 ml BHI medium contained in 100 ml Erlenmeyer flasks with 3 baffles. To isolate clones that have encountered a second recombination event, an aliquot was taken from each liquid culture, suitably diluted and plated (typically 100 to 200 µl) on BHI agar supplemented with 10% saccharose. These agar plates were incubated for 48 h at 33° C. Colonies growing on the saccharose containing agar plates were then examined for kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Clones that proved to be sensitive to kanamycin and resistant to saccharose were examined by PCR and DNA sequencing for the appropriate integration of the sod promoter. The resulting strain was named ATCC13032_Psod-carAB_DaceB.

TABLE 9

| List of strains | |
| --- | --- |
| Strain | Comment |
| *Escherichia coli* | |
| NEB ® Stable | Commercial cloning strain (New England BioLabs Inc., Ipswich, USA) |

TABLE 9-continued

List of strains

| Strain | Comment |
|---|---|
| *Corynebacterium glutamicum* | |
| ATCC13032 | *Corynebacterium glutamicum* wild type strain (Kinoshita et al., 1957*) |
| ATCC13032_Psod-carAB | Increased ability to produce L-arginine due to chromosomal integration of the strong sod promotor upstream of carAB in *C. glutamicum* ATCC13032 |
| ATCC13032_Psod-carAB_DaceB | Chromosomal deletion of the aceB gene and chromosomal integration of the strong sod promotor upstream of carAB in *C. glutamicum* ATCC13032 |

*)Kinoshita S, Udaka S, Shimono M., J. Gen. Appl. Microbiol. 1957; 3(3): 193-205.

Example 9: Transformation of *C. glutamicum* Strains with Various Expression Plasmids The following strains of *C. glutamicum* were transformed with plasmids by electroporation (Table 10). Plasmid containing cells were selected with 25 mg/l kanamycin.

- *C. glutamicum* ATCC13032: commonly used wild type strain (Kinoshita et al., J. Gen. App. Microbiol. 1957; 3(3): 193-205)
- *C. glutamicum* ATCC13032_Psod-carAB: Increased ability to produce L-arginine due to the chromosomal integration of the strong sod promotor upstream of carAB in ATCC13032
- *C. glutamicum* ATCC13032_Psod-carAB_DaceB: reduced activity of malate synthase due to the chromosomal deletion of the aceB gene and increased ability to produce L-arginine due to the chromosomal integration of the strong sod promotor upstream of carAB in ATCC13032

TABLE 10

List of plasmid-containing *C. glutamicum* strains

| Plasmid | Recipient strain | Resulting strain |
|---|---|---|
| pEC-XK99E | ATCC13032 | ATCC13032/pEC-XK99E |
| pEC-XK99E_AGAT_Mp | ATCC13032 | ATCC13032/pEC-XK99E_AGAT_Mp |
| pEC-XK99E_AGAT_Mp_AtGGT1 | ATCC13032 | ATCC13032/pEC-XK99E_AGAT_Mp_AtGGT1 |
| pEC-XK99E_AGAT_Mp_AtGGT2 | ATCC13032 | ATCC13032/pEC-XK99E_AGAT_Mp_AtGGT2 |
| pEC-XK99E_AGAT_Mp_AGT_TI | ATCC13032 | ATCC13032/pEC-XK99E_AGAT_Mp_AGT_TI |
| pEC-XK99E_AGAT_Mp_AtGGT1 | ATCC13032_Psod-carAB | ATCC13032_Psod-carAB/pEC-XK99E_AGAT_Mp_AtGGT1 |
| pEC-XK99E_AGAT_Mp_AtGGT2 | ATCC13032_Psod-carAB | ATCC13032_Psod-carAB/pEC-XK99E_AGAT_Mp_AtGGT2 |
| pEC-XK99E_AGAT_Mp_AGT_TI | ATCC13032_Psod-carAB | ATCC13032_Psod-carAB/pEC-XK99E_AGAT_Mp_AGT_TI |
| pEC-XK99E_AGAT_Mp_AtGGT1 | ATCC13032_Psod-carAB_DaceB | ATCC13032_Psod-carAB_DaceB/pEC-XK99E_AGAT_Mp_AtGGT1 |
| pEC-XK99E_AGAT_Mp_AtGGT2 | ATCC13032_Psod-carAB_DaceB | ATCC13032_Psod-carAB_DaceB/pEC-XK99E_AGAT_Mp_AtGGT2 |
| pEC-XK99E_AGAT_Mp_AGT_TI | ATCC13032_Psod-carAB_DaceB | ATCC13032_Psod-carAB_DaceB/pEC-XK99E_AGAT_Mp_AGT_TI |

Example 10: Impact of Increased Activity of a Glyoxylate Aminotransferase on GAA Production To assess the impact of an increased enzymatic activity of a glyoxylate aminotransferase on GAA production, strains ATCC13032/pEC-XK99E, ATCC13032/pEC-XK99E_AGAT_Mp, ATCC13032/pEC-XK99E_AGAT_Mp_AtGGT1, ATCC13032/pEC-XK99E_AGAT_Mp_AtGGT2, and ATCC13032/pEC-XK99E_AGAT_Mp_AGT_TI were cultivated in the Wouter Duetz system, and the resulting GAA titers were determined. The production medium (PM) contained 40 g/l D-glucose and 1.90 g/L L-arginine, but no additional glycine.

TABLE 11

Impact of increased enzymatic activity of a glyoxylate aminotransferase on GAA production in the presence of 1.90 g/L L-arginine.

| Strain | GAA |
|---|---|
| ATCC13032/pEC-XK99E | not detectable |
| ATCC13032/pEC-XK99E_AGAT_Mp | 122 mg/L |
| ATCC13032/pEC-XK99E_AGAT_Mp_AtGGT1 | 246 mg/L |
| ATCC13032/pEC-XK99E_AGAT_Mp_AtGGT2 | 255 mg/L |
| ATCC13032/pEC-XK99E_AGAT_Mp_AGT_TI | 199 mg/L |

As shown in table 11, strain ATCC13032/pEC-XK99E did not produce a detectable amount of GAA.

Strain ATCC13032/pEC-XK99E_AGAT_Mp has a polynucleotide coding for the AGAT from *Moorea producens*, which provides enzymatic AGAT activity. It produced 122 mg/L of GAA.

Strains ATCC13032/pEC-XK99E_AGAT_Mp_AtGGT1, ATCC13032/pEC-XK99E_AGAT_Mp_AtGGT2, and ATCC13032/pEC-XK99E_AGAT_Mp_AGT_TI have enzymatic AGAT activity and an increased enzymatic activity of glyoxylate aminotransferases. They produced 248 mg/l, 255 mg/l, and 199 mg/l of GAA respectively.

We conclude that, in the presence of enzymatic AGAT activity, increased enzymatic activity of a glyoxylate aminotransferase improves GAA production.

Example 11: Impact of Increased Activity of a Glyoxylate Aminotransferase Combined with Increased Ability to Produce L-Arginine on GAA Production To assess the impact of increased activity of a glyoxylate aminotransferase combined with an increased ability to produce L-arginine on GAA production, strains ATCC13032/pEC-XK99E_AGAT_Mp_AtGGT1, ATCC13032/pEC-XK99E_AGAT_Mp_AtGGT2, ATCC13032/pEC-XK99E_AGAT_Mp_AGT_TI, ATCC13032_Psod-carAB/pEC-XK99E_AGAT_Mp_AtGGT1, ATCC13032_Psod-carAB/pEC-XK99E_AGAT_Mp_AtGGT2, and ATCC13032_Psod-carAB/pEC-XK99E_AGAT_Mp_AGT_TI were cultivated in the Wouter Duetz system, and the resulting GAA titers were determined. Due to the insertion of the strong sod-promoter upstream of the cromosomal genes carA and carB, the latter three strains have an improved ability to produce L-arginine. The production medium (PM) contained 40 g/l D-glucose and 1.90 g/L L-arginine, but no additional glycine.

TABLE 12

Impact of increased activity of glyoxylate aminotransferases combined with increased ability to produce L-arginine on GAA production in the presence of 1.90 g/L L-arginine.

| Strain | GAA |
| --- | --- |
| ATCC13032/pEC-XK99E_AGAT_Mp_AtGGT1 | 246 mg/L |
| ATCC13032/pEC-XK99E_AGAT_Mp_AtGGT2 | 255 mg/L |
| ATCC13032/pEC-XK99E_AGAT_Mp_AGT_TI | 199 mg/L |
| ATCC13032_Psod-carAB/pEC-XK99E_AGAT_Mp_AtGGT1 | 325 mg/L |
| ATCC13032_Psod-carAB/pEC-XK99E_AGAT_Mp_AtGGT2 | 322 mg/L |
| ATCC13032_Psod-carAB/pEC-XK99E_AGAT_Mp_AGT_TI | 316 mg/L |

Strains ATCC13032/pEC-XK99E_AGAT_Mp_AtGGT1, ATCC13032/pEC-XK99E_AGAT_Mp_AtGGT2, and ATCC13032/pEC-XK99E_AGAT_Mp_AGT_TI have enzymatic AGAT activity and increased enzymatic activity of glyoxylate aminotransferases. As shown in table 12, they produced 248 mg/l, 255 mg/l, and 199 mg/l of GAA respectively.

Strains ATCC13032_Psod-carAB/pEC-XK99E_AGAT_Mp_AtGGT1, ATCC13032_Psod-carAB/pEC-XK99E_AGAT_Mp_AtGGT2, and ATCC13032_Psod-carAB/pEC-XK99E_AGAT_Mp_AGT_TI also have enzymatic AGAT activity and an increased enzymatic activity of a glyoxylate aminotransferase. In addition, they have an increased ability to produce L-arginine. These strains produced 325 mg/l, 322 mg/l, and 316 mg/l of GAA respectively.

We conclude that, in the presence of enzymatic AGAT activity, the combination of increased activity of a glyoxylate aminotransferase and increased ability to produce L-arginine improves GAA production.

Example 12: Combined Impact of Increased Glyoxylate Aminotransferase Activity, Reduced Malate Synthase Activity, and Increased Ability to Produce L-Arginine on GAA Production To assess the combined impact of increased glyoxylate aminotransferase activity, reduced malate synthase activity, and increased ability to produce L-arginine on GAA production, strains ATCC13032_Psod-carAB/pEC-XK99E_AGAT_Mp_AtGGT1, ATCC13032_Psod-carAB/pEC-XK99E_AGAT_Mp_AtGGT2, ATCC13032_Psod-carAB/pEC-XK99E_AGAT_Mp_AGT_TI, ATCC13032_Psod-carAB_DaceB/pEC-XK99E_AGAT_Mp_AtGGT1, ATCC13032_Psod-carAB_DaceB/pEC-XK99E_AGAT_Mp_AtGGT2, and ATCC13032_Psod-carAB_DaceB/pEC-XK99E_AGAT_Mp_AGT_TI were cultivated in the Wouter Duetz system, and the resulting GAA titers were determined. Due to the deletion of the aceB gene, the latter three strains have reduced malate synthase activity. The production medium (PM) contained 40 g/l D-glucose and 1.90 g/L L-arginine, but no additional glycine.

TABLE 13

Combined impact of increased glyoxylate aminotransferase activity, reduced malate synthase activity, and increased ability to produce L-arginine on GAA production in the presence of 1.9 g/L L-arginine.

| Strain | GAA |
| --- | --- |
| ATCC13032_Psod-carAB/pEC-XK99E_AGAT_Mp_AtGGT1 | 325 mg/L |
| ATCC13032_Psod-carAB/pEC-XK99E_AGAT_Mp_AtGGT2 | 322 mg/L |
| ATCC13032_Psod-carAB/pEC-XK99E_AGAT_Mp_AGT_TI | 316 mg/L |
| ATCC13032_Psod-carAB_DaceB/pEC-XK99E_AGAT_Mp_AtGGT1 | 362 mg/L |
| ATCC13032_Psod-carAB_DaceB/pEC-XK99E_AGAT_Mp_AtGGT2 | 354 mg/L |
| ATCC13032_Psod-carAB_DaceB/pEC-XK99E_AGAT_Mp_AGT_TI | 331 mg/L |

Strains ATCC13032-Psod-carAB/pEC-XK99E_AGAT_Mp_AtGGT1, ATCC13032_Psod-carAB/pEC-XK99E_AGAT_Mp_AtGGT2, and ATCC13032-Psod-carAB/pEC-XK99E_AGAT_Mp_AGT_TI have enzymatic AGAT activity, increased enzymatic activity of glyoxylate aminotransferases, and an increased ability to produce L-arginine. As shown in table 13, these strains produced 325 mg/l, 322 mg/l, and 316 mg/l of GAA respectively.

Strains ATCC13032_Psod-carAB_DaceB/pEC-XK99E_AGAT_Mp_AtGGT1, ATCC13032_Psod-carAB_DaceB/pEC-XK99E_AGAT_Mp_AtGGT2, and ATCC13032_Psod-carAB_DaceB/pEC-XK99E_AGAT_Mp_AGT_TI also have enzymatic AGAT activity, increased enzymatic activity of glyoxylate aminotransferases, and an increased ability to produce L-arginine. In addition, they have a reduced enzymatic activity of the malate synthase. These strains produced 362 mg/l, 354 mg/l, and 331 mg/l of GAA respectively.

We conclude that the combination of enzymatic AGAT activity, increased glyoxylate aminotransferase activity, reduced malate synthase activity, and an increased ability to produce L-arginine improves the production of GAA.

The invention claimed is:

1. A microorganism, comprising:
   at least one gene coding for a protein having the function of a L-arginine:glycine amidinotransferase, and
   at least one protein having the function of a glyoxylate aminotransferase,
   wherein the at least one protein having the function of the glyoxylate aminotransferase comprises an amino acid sequence which is at least 80% homologous to an amino acid sequence selected from the group of: SEQ ID NO:2, SEQ ID NO:5, and SEQ ID NO:8, and
   wherein the protein having the function of the L-arginine;olycine amidinotransferase comprises an amino acid sequence which is at least 80% homologous to the amino acid sequence according to SEQ ID NO: 11.

2. The microorganism of claim 1, wherein an enzymic activity of the at least one protein having the function of the glyoxylate aminotransferase is increased compared to a respective enzymic activity in a wildtype microorganism.

3. The microorganism of claim 1, wherein the microorganism has an increased ability to produce L-arginine compared with an ability of a wildtype microorganism.

4. The microorganism of claim 3, wherein the microorganism has increased activity of an enzyme having a function of a carbamoylphosphate synthase compared to the respective enzymic activity in the wildtype microorganism.

5. The microorganism of claim 3, wherein the microorganism further comprises an enzyme having a function of an argininosuccinate lyase with an increased activity compared to the respective enzymic activity in the wildtype microorganism.

6. The microorganism of claim 3, wherein the microorganism further comprises an enzyme having a function of an ornithine carbamoyltransferase with an increased activity compared to the respective enzymic activity in the wildtype microorganism.

7. The microorganism of claim 3, wherein the microorganism further comprises an enzyme having a function of an argininosuccinate synthetase with an increased activity compared to the respective enzymic activity in the wildtype microorganism.

8. The microorganism of claim 3, wherein increased activity of an enzyme is achieved by overexpressing a gene encoding the respective enzyme.

9. The microorganism of claim 3, wherein activity of a protein having a function of a malate synthase is decreased compared to the respective activity in the wildtype microorganism.

10. The microorganism of claim 9, wherein an expression of a gene encoding the protein having the function of the malate synthase is attenuated compared to the expression of the respective gene in the wildtype microorganism, or
    wherein the gene encoding the protein having the function of the malate synthase is deleted.

11. The microorganism of claim 3, wherein an arginine operon (argCJBDFR) is overexpressed.

12. The microorganism of claim 3, wherein an expression of an argR gene coding for an arginine responsive repressor protein ArgR is attenuated compared to the expression of the argR gene in the wildtype microorganism, or
    wherein the argR gene is deleted.

13. The microorganism of claim 3, wherein at least one or more of a gene coding for an enzyme of a biosynthetic pathway of L-arginine is overexpressed, the at least one or more of a gene comprising gdh, argJ, argB, argC, and/or argD coding for a glutamate dehydrogenase, for an ornithine acetyltransferase, for an acetylglutamate kinase, for an acetylglutamylphosphate reductase, and for an acetylornithine aminotransferase, respectively.

14. The microorganism of claim 1, wherein the at least one gene coding for the protein having the function of the L-arginine: glycine amidinotransferase is heterologous.

15. The microorganism of claim 1, wherein the at least one gene coding for the protein having the function of the L-arginine:glycine amidinotransferase is overexpressed.

16. The microorganism of claim 1, wherein the microorganism belongs to the genus *Corynebacterium*, to the genus Enterobacteriaceae, or to the genus *Pseudomonas*.

17. The microorganism of claim 16, wherein the microorganism is *Corynebacterium glutamicum*.

18. The microorganism of claim 16 wherein the microorganism is *Escherichia coli*.

19. The microorganism of claim 16 wherein the microorganism is *Pseudomonas putida*.

20. A method for the fermentative production of guanidino acetic acid (GAA), comprising:
  a) cultivating the microorganism as defined in claim 1 in a suitable medium under suitable conditions, and
  b) accumulating GAA in the medium to form a GAA containing fermentation broth.

21. The method of claim 20, further comprising:
  isolating GAA from the GAA containing fermentation broth.

22. The method of claim 20, further comprising:
  drying and/or granulating the GAA containing fermentation broth.

23. The microorganism as claimed in claim 1, further comprising a gene coding for an enzyme having an activity of a guanidinoacetate N-methyltransferase.

24. The microorganism of claim 23, wherein the gene coding for the enzyme having the activity of the guanidinoacetate N-methyltransferase is overexpressed.

25. A method for the fermentative production of creatine, comprising:
  a) cultivating the microorganism as defined in claim 23 in a suitable medium under suitable conditions, and
  b) accumulating creatine in the medium to form a creatine containing fermentation broth.

26. The method of claim 25, further comprising:
  isolating creatine from the creatine containing fermentation broth.

27. The microorganism of claim 1, wherein the amino acid sequence is at least 90% homologous to the amino acid sequence selected from the group of: SEQ ID NO:2, SEQ ID NO:5, and SEQ ID NO:8.

28. The microorganism of claim 27, wherein the amino acid sequence is at least 90% homologous to the amino acid sequence according to SEQ ID NO:11.

* * * * *

SEQUENCE LISTING

<160> NUMBER OF SEQ ID NOS: 23

<210> SEQ ID NO 1
<211> LENGTH: 2205
<212> TYPE: DNA
<213> ORGANISM: Arabidopsis thaliana
<220> FEATURE:
<221> NAME/KEY: CDS
<222> LOCATION: (425)..(1870)
<223> OTHER INFORMATION: GGT1

<400> SEQUENCE: 1

```
ctcttcgtct ggaatctcca ccacattttt attctcttca aaaattatct gcttctattt      60
ttataattaa gcaagaacgg tcttcgtagc ataaaaacga gacacggata tagagatatc     120
gtgaattgac ttttgtctga caaatcctct tcgtcaattt cagtggctct gctgcttcct     180
ttgttgtgaa gccacataga ttagattgag gaatgatcca aactcatgtc atacacacat     240
ttgtaatctg ctacacaaaa tacttttaaa atcacacaca ctaatatttt aactctcccc     300
actctttgcc ttgcccttgg ctctagaacc gaacgtgact ctccagatag acttttggag     360
tcacaacatt gagtttgaag aggagggaag aagtgagcta gggattggtt cagagtgaac     420 ataa atg gct ctc aag gca tta gac tac gat act ctg aat gaa aac gtc      469
     Met Ala Leu Lys Ala Leu Asp Tyr Asp Thr Leu Asn Glu Asn Val
     1               5                  10                  15 aag aag tgt cag tat gcc gta aga ggt gaa ctt tat ctc cga gct tct      517
Lys Lys Cys Gln Tyr Ala Val Arg Gly Glu Leu Tyr Leu Arg Ala Ser
                20                  25                  30 gag ctg cag aaa gaa ggc aaa aag att att ttc aca aac gtt ggg aac      565
Glu Leu Gln Lys Glu Gly Lys Lys Ile Ile Phe Thr Asn Val Gly Asn
            35                  40                  45 cct cat gct tta gga cag aag cca ttg aca ttt cct cgc cag gtg gtt      613
Pro His Ala Leu Gly Gln Lys Pro Leu Thr Phe Pro Arg Gln Val Val
        50                  55                  60 gcg ctt tgc caa gct ccg ttt cta cta gat gac cca aat gtt gga atg      661
Ala Leu Cys Gln Ala Pro Phe Leu Leu Asp Asp Pro Asn Val Gly Met
 65                  70                  75 cta ttt cca gct gat gct att gca aga gct aaa cat tat ctt tcc ttg      709
Leu Phe Pro Ala Asp Ala Ile Ala Arg Ala Lys His Tyr Leu Ser Leu
 80                  85                  90                  95 act tca ggc ggt tta ggt gct tac agt gat tca aga ggc ctt cca gga      757
Thr Ser Gly Gly Leu Gly Ala Tyr Ser Asp Ser Arg Gly Leu Pro Gly
                100                 105                 110 gtt agg aaa gag gtt gct gag ttc att caa cgg cgt gat ggg tat cca      805
Val Arg Lys Glu Val Ala Glu Phe Ile Gln Arg Arg Asp Gly Tyr Pro
            115                 120                 125 agt gac cca gaa ctc atc ttt ctc act gat gga gct agc aaa ggt gtg      853
Ser Asp Pro Glu Leu Ile Phe Leu Thr Asp Gly Ala Ser Lys Gly Val
        130                 135                 140 atg caa atc ttg aat tgt gtt ata cgc ggt aat gga gat ggg att cta      901
Met Gln Ile Leu Asn Cys Val Ile Arg Gly Asn Gly Asp Gly Ile Leu
145                 150                 155 gtt ccg gtt cca cag tat cca ctt tac tca gct acc ata tca ctg tta      949
Val Pro Val Pro Gln Tyr Pro Leu Tyr Ser Ala Thr Ile Ser Leu Leu
160                 165                 170                 175 ggt ggt act ctt gtt cct tac tat ctt gat gag tct gaa aac tgg gga      997
Gly Gly Thr Leu Val Pro Tyr Tyr Leu Asp Glu Ser Glu Asn Trp Gly
                180                 185                 190 ctt gat gtt gct aac ctt cga caa tcc gtt gct cag gct cgt tct caa     1045
Leu Asp Val Ala Asn Leu Arg Gln Ser Val Ala Gln Ala Arg Ser Gln
            195                 200                 205
```

-continued

```
ggg ata aca gta agg gca atg gtg atc att aac cct ggg aac cca act    1093
Gly Ile Thr Val Arg Ala Met Val Ile Ile Asn Pro Gly Asn Pro Thr
        210                 215                 220 ggc cag tgt cta agc gaa gct aac ata aga gag ata ttg aag ttc tgt    1141
Gly Gln Cys Leu Ser Glu Ala Asn Ile Arg Glu Ile Leu Lys Phe Cys
    225                 230                 235 tat aac gag aaa ctg gtt ctt ctg gga gac gag gtt tat cag cag aac    1189
Tyr Asn Glu Lys Leu Val Leu Leu Gly Asp Glu Val Tyr Gln Gln Asn
240                 245                 250                 255 ata tac cag gat gag cgt ccc ttt atc agc tcc aag aag gtt ttg atg    1237
Ile Tyr Gln Asp Glu Arg Pro Phe Ile Ser Ser Lys Lys Val Leu Met
                260                 265                 270 gaa atg ggt tcg ccg ttc agc aag gaa gtt cag ctt gta tct ttt cac    1285
Glu Met Gly Ser Pro Phe Ser Lys Glu Val Gln Leu Val Ser Phe His
                275                 280                 285 aca gtc tct aaa gga tat tgg ggt gaa tgt gga cag cga ggt gga tac    1333
Thr Val Ser Lys Gly Tyr Trp Gly Glu Cys Gly Gln Arg Gly Gly Tyr
            290                 295                 300 ttt gag atg acc aac ctc cct cca agg gtt gtt gag gag ata tac aag    1381
Phe Glu Met Thr Asn Leu Pro Pro Arg Val Val Glu Glu Ile Tyr Lys
    305                 310                 315 gtt gca tca att gcc ctc agc cct aat gtc tct gcg caa atc ttt atg    1429
Val Ala Ser Ile Ala Leu Ser Pro Asn Val Ser Ala Gln Ile Phe Met
320                 325                 330                 335 ggt ttg atg gtt aat cct cca aag cct gga gac att tca tat gac cag    1477
Gly Leu Met Val Asn Pro Pro Lys Pro Gly Asp Ile Ser Tyr Asp Gln
                340                 345                 350 ttc gcc cgt gaa agc aag ggg att ctt gaa tct ttg aga aga aga gca    1525
Phe Ala Arg Glu Ser Lys Gly Ile Leu Glu Ser Leu Arg Arg Arg Ala
                355                 360                 365 agg ctc atg aca gat gga ttc aac agc tgc aaa aac gtc gtg tgc aat    1573
Arg Leu Met Thr Asp Gly Phe Asn Ser Cys Lys Asn Val Val Cys Asn
            370                 375                 380 ttc aca gaa ggt gca atg tat tcg ttt cct caa ata cgg tta cca acg    1621
Phe Thr Glu Gly Ala Met Tyr Ser Phe Pro Gln Ile Arg Leu Pro Thr
    385                 390                 395 gga gct ctc caa gct gca aaa caa gct gga aaa gtg cca gac gtt ttc    1669
Gly Ala Leu Gln Ala Ala Lys Gln Ala Gly Lys Val Pro Asp Val Phe
400                 405                 410                 415 tac tgt ctc aag ctc tta gaa gcc aca gga atc tcc aca gta cct ggc    1717
Tyr Cys Leu Lys Leu Leu Glu Ala Thr Gly Ile Ser Thr Val Pro Gly
                420                 425                 430 tct gga ttt gga cag aaa gaa ggt gtg ttc cat ctg agg aca aca atc    1765
Ser Gly Phe Gly Gln Lys Glu Gly Val Phe His Leu Arg Thr Thr Ile
                435                 440                 445 ctg cca gca gaa gat gag atg ccg gag atc atg gat agc ttc aag aag    1813
Leu Pro Ala Glu Asp Glu Met Pro Glu Ile Met Asp Ser Phe Lys Lys
            450                 455                 460 ttc aac gac gag ttc atg act cag tat gat aat aac ttt ggt tat tcg    1861
Phe Asn Asp Glu Phe Met Thr Gln Tyr Asp Asn Asn Phe Gly Tyr Ser
    465                 470                 475 aaa atg tga ttacttcttc ttctgaacga ctattgtgtt ctgctacact            1910
Lys Met
480 ctttaaagct aaatctctgt agtacactct ttctctttgc cctattctat aaaccatatc  1970 tctctctttg tgtctctttt ttttgggtgt aaactctctc ttgtgtctct atttctattt  2030 tcaattggaa actgattaag atcttttctc aatgaaatga agtttaggcc atagattatt  2090
```

```
tttttttaatc aacggtgata gccttttttt agtgtggcaa tgtgaaattt gtaattatgc     2150
taattatatt aaagaaaata ataataatcc atgtcctagt ttgttttga ttatg            2205
```

<210> SEQ ID NO 2
<211> LENGTH: 481
<212> TYPE: PRT
<213> ORGANISM: Arabidopsis thaliana

<400> SEQUENCE: 2

```
Met Ala Leu Lys Ala Leu Asp Tyr Asp Thr Leu Asn Glu Asn Val Lys
1               5                   10                  15

Lys Cys Gln Tyr Ala Val Arg Gly Glu Leu Tyr Leu Arg Ala Ser Glu
            20                  25                  30

Leu Gln Lys Glu Gly Lys Lys Ile Ile Phe Thr Asn Val Gly Asn Pro
        35                  40                  45

His Ala Leu Gly Gln Lys Pro Leu Thr Phe Pro Arg Gln Val Val Ala
    50                  55                  60

Leu Cys Gln Ala Pro Phe Leu Asp Asp Pro Asn Val Gly Met Leu
65                  70                  75                  80

Phe Pro Ala Asp Ala Ile Ala Arg Ala Lys His Tyr Leu Ser Leu Thr
                85                  90                  95

Ser Gly Gly Leu Gly Ala Tyr Ser Asp Ser Arg Gly Leu Pro Gly Val
            100                 105                 110

Arg Lys Glu Val Ala Glu Phe Ile Gln Arg Arg Asp Gly Tyr Pro Ser
        115                 120                 125

Asp Pro Glu Leu Ile Phe Leu Thr Asp Gly Ala Ser Lys Gly Val Met
    130                 135                 140

Gln Ile Leu Asn Cys Val Ile Arg Gly Asn Gly Asp Gly Ile Leu Val
145                 150                 155                 160

Pro Val Pro Gln Tyr Pro Leu Tyr Ser Ala Thr Ile Ser Leu Leu Gly
                165                 170                 175

Gly Thr Leu Val Pro Tyr Tyr Leu Asp Glu Ser Glu Asn Trp Gly Leu
            180                 185                 190

Asp Val Ala Asn Leu Arg Gln Ser Val Ala Gln Ala Arg Ser Gln Gly
        195                 200                 205

Ile Thr Val Arg Ala Met Val Ile Asn Pro Gly Asn Pro Thr Gly
    210                 215                 220

Gln Cys Leu Ser Glu Ala Asn Ile Arg Glu Ile Leu Lys Phe Cys Tyr
225                 230                 235                 240

Asn Glu Lys Leu Val Leu Leu Gly Asp Glu Val Tyr Gln Gln Asn Ile
                245                 250                 255

Tyr Gln Asp Glu Arg Pro Phe Ile Ser Ser Lys Lys Val Leu Met Glu
            260                 265                 270

Met Gly Ser Pro Phe Ser Lys Glu Val Gln Leu Val Ser Phe His Thr
        275                 280                 285

Val Ser Lys Gly Tyr Trp Gly Glu Cys Gly Gln Arg Gly Gly Tyr Phe
    290                 295                 300

Glu Met Thr Asn Leu Pro Pro Arg Val Val Glu Glu Ile Tyr Lys Val
305                 310                 315                 320

Ala Ser Ile Ala Leu Ser Pro Asn Val Ser Ala Gln Ile Phe Met Gly
                325                 330                 335

Leu Met Val Asn Pro Pro Lys Pro Gly Asp Ile Ser Tyr Asp Gln Phe
            340                 345                 350

Ala Arg Glu Ser Lys Gly Ile Leu Glu Ser Leu Arg Arg Arg Ala Arg
```

| | 355 | | | | 360 | | | | 365 | | |
|---|---|---|---|---|---|---|---|---|---|---|---|
| Leu | Met | Thr | Asp | Gly | Phe | Asn | Ser | Cys | Lys | Asn | Val | Val | Cys | Asn | Phe |
| 370 | | | | | 375 | | | | 380 | | |

Thr Glu Gly Ala Met Tyr Ser Phe Pro Gln Ile Arg Leu Pro Thr Gly
385   390   395   400

Ala Leu Gln Ala Ala Lys Gln Ala Gly Lys Val Pro Asp Val Phe Tyr
      405   410   415

Cys Leu Lys Leu Leu Glu Ala Thr Gly Ile Ser Thr Val Pro Gly Ser
      420   425   430

Gly Phe Gly Gln Lys Glu Gly Val Phe His Leu Arg Thr Thr Ile Leu
      435   440   445

Pro Ala Glu Asp Glu Met Pro Glu Ile Met Asp Ser Phe Lys Lys Phe
      450   455   460

Asn Asp Glu Phe Met Thr Gln Tyr Asp Asn Asn Phe Gly Tyr Ser Lys
465   470   475   480

Met

<210> SEQ ID NO 3
<211> LENGTH: 1560
<212> TYPE: DNA
<213> ORGANISM: Artificial Sequence
<220> FEATURE:
<223> OTHER INFORMATION: construct AtGGT1_opt_RBS

<400> SEQUENCE: 3

```
ggtctcccaa gcttgcatgc ctgcaggtcg actctagagg atccgacgtc aggaaaggag      60
aggattgatg gcgctgaagg ccctcgatta cgacacgctg aatgagaacg tcaaaaaatg     120
ccaatatgct gtgcggggcg agttgtatct tcgtgcctcc gagctgcaaa agagggcaa      180
aaagattatt ttcaccaacg taggaaatcc tcacgccttg gccagaagc cacttacgtt      240
cccgcggcaa gttgttgcgc tttgccaagc accattcctg ctggatgatc taacgtagg     300
tatgttgttc ccggctgacg cgattgcccg ggctaagcat tacctgtctc tgacttcggg     360
tggtcttggc gcttactcgg attcacgcgg cttgccaggt gtccgaaaag aggtggctga     420
gtttattcaa cggcgggacg gctacccatc agaccctgaa ctcatctttc ttacggatgg     480
tgcttctaaa ggtgtaatgc aaattctcaa ctgtgtgatt cgcggtaatg agatggtat     540
ccttgtcccg gtcccacagt atccactgta ctccgcgact atttctcttc tcggcggaac     600
gctggttccg tattatttgg acgaatcgga gaattggggc ctcgacgtag ccaaccttcg     660
tcagagcgtc gcacaggcgc gttcacaagg catcactgtc cgggcgatgg ttattattaa     720
cccgggaaac ccgactggac aatgcttgag cgaagcaaat attcgtgaga tccttaaatt     780
ttgctacaac gagaagctgg tactcctcgg agatgaggtt taccaacaaa acattttatca    840
ggatgaacgg ccttttatct cgtcaaagaa ggtactgatg gagatgggtt ctccttttcag    900
caaagaagta cagctggtca gcttccatac tgtctctaag ggttattggg gtgaatgtgg    960
ccagcgcggc ggctacttcg aaatgactaa cctcccccct cgcgtcgtgg aagagatcta   1020
taaggttgca tctattgctt tgtcgcccaa cgtatcggcc cagatctta tgggactgat   1080
ggtaaacccc cctaaacctg gagacattag ctacgaccag ttcgcgcgtg aatctaaggg   1140
tatccttgaa tcccttcgtc gccgcgcgcg tctgatgact gacggattca attcatgtaa   1200
gaacgtagta tgcaacttca cggaaggcgc gatgtactct ttccccccaga tccgtcttcc   1260
aaccggtgca ctccaggctg ctaagcaggc gggaaaggtg cccgatgtgt ttattgtct   1320
```

```
caaattgttg gaggcgaccg gcatctccac tgttccaggc agcggctttg acagaagga      1380 gggagttttt catctgcgta cgactatcct tcctgccgag gatgagatgc ctgaaattat      1440
ggattctttc aagaagttta cgacgagtt catgactcaa tatgacaata atttcggata       1500
ctccaaaatg taataaggat ccccgggtac cgagctcgaa ttcactggcc gtcggagacc      1560

<210> SEQ ID NO 4
<211> LENGTH: 1817
<212> TYPE: DNA
<213> ORGANISM: Arabidopsis thaliana
<220> FEATURE:
<221> NAME/KEY: CDS
<222> LOCATION: (148)..(1593)
<223> OTHER INFORMATION: GGT2

<400> SEQUENCE: 4
ataaaaaacc aatctttatg atcgactcaa taagtcaaat cttgttgtgt taagtgaaat       60
ctatagtagt gaaagggtct ccacttagct gtttgagggg aagtgaggaa tcattttgct      120
tttagctttg aaaagtaaat cctggaa atg tct ctc aag gcg tta gac tac gag      174
                                Met Ser Leu Lys Ala Leu Asp Tyr Glu
                                  1               5 tcc ttg aat gaa aac gtg aag aat tgt cag tat gca gtc aga ggt gaa          222
Ser Leu Asn Glu Asn Val Lys Asn Cys Gln Tyr Ala Val Arg Gly Glu
 10                  15                  20                  25 ctt tat ctt cgt gct tct gag ctt cag aaa gaa ggc aaa aag att att          270
Leu Tyr Leu Arg Ala Ser Glu Leu Gln Lys Glu Gly Lys Lys Ile Ile
                 30                  35                  40 ttc aca aat gtt gga aac cct cat gct tta gga cag aaa cct ctg act          318
Phe Thr Asn Val Gly Asn Pro His Ala Leu Gly Gln Lys Pro Leu Thr
             45                  50                  55 ttt cct cgt cag gtg gtt tct tta tgc caa gca cca ttt ctg tta gat          366
Phe Pro Arg Gln Val Val Ser Leu Cys Gln Ala Pro Phe Leu Leu Asp
         60                  65                  70 gat cca aat gtt ggt atg ata ttc cca gca gat gct att gca aga gct          414
Asp Pro Asn Val Gly Met Ile Phe Pro Ala Asp Ala Ile Ala Arg Ala
     75                  80                  85 aag cat tat ctt tcc ttg act tct ggt ggt ctt ggt gct tac agt gac          462
Lys His Tyr Leu Ser Leu Thr Ser Gly Gly Leu Gly Ala Tyr Ser Asp
 90                  95                 100                 105 tca aga ggt ctt ccg gga gtt cgg aaa gaa gtc gct gag ttc att gaa          510
Ser Arg Gly Leu Pro Gly Val Arg Lys Glu Val Ala Glu Phe Ile Glu
                110                 115                 120 cgg cgt gat gga tat cca agc gat cca gaa ctc ata ttt cta act gat          558
Arg Arg Asp Gly Tyr Pro Ser Asp Pro Glu Leu Ile Phe Leu Thr Asp
            125                 130                 135 gga gcg agc aaa ggt gtg atg caa atc ttg aat tgt gtc ata cgc ggt          606
Gly Ala Ser Lys Gly Val Met Gln Ile Leu Asn Cys Val Ile Arg Gly
        140                 145                 150 cag aaa gac gga att ctg gtt cca gtt cca cag tat cca ctc tac tcg          654
Gln Lys Asp Gly Ile Leu Val Pro Val Pro Gln Tyr Pro Leu Tyr Ser
    155                 160                 165 gct act ata tct ctg tta ggt ggt act ctt gtt cct tac tat ctt gaa          702
Ala Thr Ile Ser Leu Leu Gly Gly Thr Leu Val Pro Tyr Tyr Leu Glu
170                 175                 180                 185 gag tct gaa aac tgg gga ctt gat gtt aac aac ctt cgc caa tct gtt          750
Glu Ser Glu Asn Trp Gly Leu Asp Val Asn Asn Leu Arg Gln Ser Val
                190                 195                 200 gct caa gct cgc tct caa gga ata aca gta agg gca atg gtg att att          798
Ala Gln Ala Arg Ser Gln Gly Ile Thr Val Arg Ala Met Val Ile Ile
            205                 210                 215
```

```
aac ccc gga aac cca act ggc cag tgt ctt agc gaa gct aac ata aga      846
Asn Pro Gly Asn Pro Thr Gly Gln Cys Leu Ser Glu Ala Asn Ile Arg
        220                 225                 230 gag ata cta cgg ttc tgt tgt gat gag aga tta gtt ctt ctc gga gac      894
Glu Ile Leu Arg Phe Cys Cys Asp Glu Arg Leu Val Leu Leu Gly Asp
    235                 240                 245 gaa gtg tat cag caa aat ata tac caa gat gaa cgt ccc ttt atc agt      942
Glu Val Tyr Gln Gln Asn Ile Tyr Gln Asp Glu Arg Pro Phe Ile Ser
250                 255                 260                 265 tcc aag aag gtt ttg atg gat atg gga gca ccg atc agc aag gaa gtt      990
Ser Lys Lys Val Leu Met Asp Met Gly Ala Pro Ile Ser Lys Glu Val
                270                 275                 280 cag ctc ata tct ttc cac acc gtt tcc aaa gga tac tgg ggc gaa tgt     1038
Gln Leu Ile Ser Phe His Thr Val Ser Lys Gly Tyr Trp Gly Glu Cys
            285                 290                 295 ggg caa cgg gga ggt tac ttt gag atg aca aat atc cct ccc agg acc     1086
Gly Gln Arg Gly Gly Tyr Phe Glu Met Thr Asn Ile Pro Pro Arg Thr
        300                 305                 310 gtt gag gag ata tac aag gtg gcc tct ata gct ctc agc ccc aac gtc     1134
Val Glu Glu Ile Tyr Lys Val Ala Ser Ile Ala Leu Ser Pro Asn Val
    315                 320                 325 tct gcg cag ata ttt atg ggt tta atg gtt agc cca cca aag cct gga     1182
Ser Ala Gln Ile Phe Met Gly Leu Met Val Ser Pro Pro Lys Pro Gly
330                 335                 340                 345 gac att tca tat gac caa ttc gtt cgt gag agc aag gga ata cta gaa     1230
Asp Ile Ser Tyr Asp Gln Phe Val Arg Glu Ser Lys Gly Ile Leu Glu
                350                 355                 360 tca ctg aga aga aga gca agg atg atg act gat gga ttc aac agc tgc     1278
Ser Leu Arg Arg Arg Ala Arg Met Met Thr Asp Gly Phe Asn Ser Cys
            365                 370                 375 aaa aac gtc gtc tgt aat ttc aca gaa ggt gct atg tat tca ttc cct     1326
Lys Asn Val Val Cys Asn Phe Thr Glu Gly Ala Met Tyr Ser Phe Pro
        380                 385                 390 caa ata aag ttg ccg tcg aaa gca atc caa gca gca aaa caa gcc gga     1374
Gln Ile Lys Leu Pro Ser Lys Ala Ile Gln Ala Ala Lys Gln Ala Gly
    395                 400                 405 aaa gtc cct gac gtt ttc tac tgc ctt aag ctc tta gaa gcc aca gga     1422
Lys Val Pro Asp Val Phe Tyr Cys Leu Lys Leu Leu Glu Ala Thr Gly
410                 415                 420                 425 atc tcc aca gtt cca ggc tct gga ttt gga caa aaa gaa ggg gtg ttt     1470
Ile Ser Thr Val Pro Gly Ser Gly Phe Gly Gln Lys Glu Gly Val Phe
                430                 435                 440 cat tta agg aca aca att ctg cca gca gaa gaa gaa atg cca gag att     1518
His Leu Arg Thr Thr Ile Leu Pro Ala Glu Glu Glu Met Pro Glu Ile
            445                 450                 455 atg gac agt ttc aaa aag ttc aat gat gag ttt atg tct cag tac gct     1566
Met Asp Ser Phe Lys Lys Phe Asn Asp Glu Phe Met Ser Gln Tyr Ala
        460                 465                 470 gat aac ttt ggt tac tcc aga atg tga aaagaaagg acttagagtc            1613
Asp Asn Phe Gly Tyr Ser Arg Met
    475                 480 agagtcagag atcacttctt cttctttcac gacattatta ttgtctattc acactcttaa   1673
aaagcaataa gtactggtcc tactctgtgt caaactcttc ttggtgctct taaaacccttt  1733 gtatctattg ttaccaattt gtgtgactca cacacacaca cacacaaatc tctaatgttc   1793
aattatatgg taaatggttt attt                                          1817
```

<210> SEQ ID NO 5

-continued

```
<211> LENGTH: 481
<212> TYPE: PRT
<213> ORGANISM: Arabidopsis thaliana

<400> SEQUENCE: 5

Met Ser Leu Lys Ala Leu Asp Tyr Glu Ser Leu Asn Glu Asn Val Lys
1               5                   10                  15

Asn Cys Gln Tyr Ala Val Arg Gly Glu Leu Tyr Leu Arg Ala Ser Glu
            20                  25                  30

Leu Gln Lys Glu Gly Lys Lys Ile Ile Phe Thr Asn Val Gly Asn Pro
        35                  40                  45

His Ala Leu Gly Gln Lys Pro Leu Thr Phe Pro Arg Gln Val Val Ser
    50                  55                  60

Leu Cys Gln Ala Pro Phe Leu Asp Asp Pro Asn Val Gly Met Ile
65                  70                  75                  80

Phe Pro Ala Asp Ala Ile Ala Arg Ala Lys His Tyr Leu Ser Leu Thr
                85                  90                  95

Ser Gly Gly Leu Gly Ala Tyr Ser Asp Ser Arg Gly Leu Pro Gly Val
            100                 105                 110

Arg Lys Glu Val Ala Glu Phe Ile Glu Arg Arg Asp Gly Tyr Pro Ser
        115                 120                 125

Asp Pro Glu Leu Ile Phe Leu Thr Asp Gly Ala Ser Lys Gly Val Met
    130                 135                 140

Gln Ile Leu Asn Cys Val Ile Arg Gly Gln Lys Asp Gly Ile Leu Val
145                 150                 155                 160

Pro Val Pro Gln Tyr Pro Leu Tyr Ser Ala Thr Ile Ser Leu Leu Gly
                165                 170                 175

Gly Thr Leu Val Pro Tyr Tyr Leu Glu Glu Ser Glu Asn Trp Gly Leu
            180                 185                 190

Asp Val Asn Asn Leu Arg Gln Ser Val Ala Gln Ala Arg Ser Gln Gly
        195                 200                 205

Ile Thr Val Arg Ala Met Val Ile Ile Asn Pro Gly Asn Pro Thr Gly
    210                 215                 220

Gln Cys Leu Ser Glu Ala Asn Ile Arg Glu Ile Leu Arg Phe Cys Cys
225                 230                 235                 240

Asp Glu Arg Leu Val Leu Leu Gly Asp Glu Val Tyr Gln Gln Asn Ile
                245                 250                 255

Tyr Gln Asp Glu Arg Pro Phe Ile Ser Ser Lys Lys Val Leu Met Asp
            260                 265                 270

Met Gly Ala Pro Ile Ser Lys Glu Val Gln Leu Ile Ser Phe His Thr
        275                 280                 285

Val Ser Lys Gly Tyr Trp Gly Glu Cys Gly Gln Arg Gly Gly Tyr Phe
    290                 295                 300

Glu Met Thr Asn Ile Pro Pro Arg Thr Val Glu Glu Ile Tyr Lys Val
305                 310                 315                 320

Ala Ser Ile Ala Leu Ser Pro Asn Val Ser Ala Gln Ile Phe Met Gly
                325                 330                 335

Leu Met Val Ser Pro Pro Lys Pro Gly Asp Ile Ser Tyr Asp Gln Phe
            340                 345                 350

Val Arg Glu Ser Lys Gly Ile Leu Glu Ser Leu Arg Arg Arg Ala Arg
        355                 360                 365

Met Met Thr Asp Gly Phe Asn Ser Cys Lys Asn Val Val Cys Asn Phe
    370                 375                 380

Thr Glu Gly Ala Met Tyr Ser Phe Pro Gln Ile Lys Leu Pro Ser Lys
```

```
                385             390             395             400
Ala Ile Gln Ala Lys Gln Ala Gly Lys Val Pro Asp Val Phe Tyr
                405                 410                 415

Cys Leu Lys Leu Leu Glu Ala Thr Gly Ile Ser Thr Val Pro Gly Ser
                420                 425                 430

Gly Phe Gly Gln Lys Glu Gly Val Phe His Leu Arg Thr Thr Ile Leu
                435                 440                 445

Pro Ala Glu Glu Met Pro Glu Ile Met Asp Ser Phe Lys Lys Phe
450                 455                 460

Asn Asp Glu Phe Met Ser Gln Tyr Ala Asp Asn Phe Gly Tyr Ser Arg
465                 470                 475                 480

Met
```

<210> SEQ ID NO 6
<211> LENGTH: 1560
<212> TYPE: DNA
<213> ORGANISM: Artificial Sequence
<220> FEATURE:
<223> OTHER INFORMATION: construct AtGGT2_opt_RBS

<400> SEQUENCE: 6

```
ggtctcccaa gcttgcatgc ctgcaggtcg actctagagg atccgacgtc aggaaaggag      60
aggattgatg tccctcaagg ctttggacta cgaatctttg aacgaaaacg ttaaaaattg     120
tcagtatgcg gtccggggtg aactctatct gcgtgcttcc gagttgcaaa agagggtaa     180
aaaaatcatt tttactaacg tcggaaaccc acacgcattg gacagaagc cacttacctt     240
tccacggcaa gttgtgtcgc tctgtcaggc tcctttttg ttggacgacc ccaacgtagg     300
tatgatcttt ccggcagatg ccatcgcccg ggcgaagcat tatttgtcac ttacctcggg     360
tggactcgga gcatattctg attcgcgggg actcccaggt gtacgtaaag aagtcgccga     420
gttcattgaa cgccgtgatg ctacccctc cgatccggaa ctcattttc ttacggacgg     480
agcgtcgaaa ggagttatgc aaattctcaa ctgtgtgatt cgcggccaga aggatggtat     540
tctggtgcca gttccgcaat accctctgta ttccgcaact atttcgctcc tcggtggaac     600
gcttgtcccc tattatttgg aggagtccga gaattgggc ctcgacgtaa ataatctgcg     660
gcaatccgtt gctcaggccc ggtcgcaggg aattactgtt cgtgcgatgg tcatcatcaa     720
tcccggcaac ccgactggac aatgcctgtc cgaggctaac attcgcgaga ttctccgttt     780
ttgctgtgac gaacggttgg ttttgcttgg agatgaagtt tatcaacaaa atatttatca     840
ggacgagcgg ccattcatca gctcaaagaa ggtattgatg gatatgggcg ctccaattag     900
caaggaggtc cagcttatct catttcacac tgtttcgaag gctactgggg cgaatgcgg     960
tcagcgggggt ggttacttcg aaatgacgaa tatccccca cgtaccgtgg aagagattta    1020
taaggttgcc tcgattgcac tttcgccaaa cgtatccgcg cagatttta tgggcctgat    1080
ggtatctccc ccaaagcccg gtgacatttc ctacgatcaa ttcgtgcggg aatcaaaagg    1140
aattcttgaa tcattgcgcc ggcgcgcccg tatgatgact gatggcttca atagctgcaa    1200
aaacgttgta tgcaacttta ccgagggtgc aatgtattct ttccctcaga ttaagctccc    1260
ttcgaaggct atccaggcgg cgaagcaagc gggaaaagtg ccagatgtct tttactgcct    1320
caaactgctg gaagcgaccg gaatctccac ggtcccgggc tctggattcg gccaaaagga    1380
aggagtattt catctccgga ctaccattct gccggcgag gaagaaatgc cagagatcat    1440
ggacagcttc aaaaaattca tgacgaatt tatgtcgcag tatgccgata acttcggcta    1500
```

-continued

```
ttcgcggatg taataaggat ccccgggtac cgagctcgaa ttcactggcc gtcggagacc      1560
```

<210> SEQ ID NO 7
<211> LENGTH: 2406
<212> TYPE: DNA
<213> ORGANISM: Thermococcus litoralis
<220> FEATURE:
<221> NAME/KEY: CDS
<222> LOCATION: (196)..(1419)
<223> OTHER INFORMATION: AGT

<400> SEQUENCE: 7

```
tctagaagca ctccccgtgg aggtgccttc ggatctttcc agagttctat ttcatagaat       60
ttctcaatca tcttaattcc attttccgga atttgtcgtg ttataaacac cttgggcttc      120
atggtatttc cccttctaag ataatggtca aaacgtataa atatcttat gaagattagt      180 taatggtgat gttga atg gat tac aca aaa tac cta gcc gga agg gcg aat      231
              Met Asp Tyr Thr Lys Tyr Leu Ala Gly Arg Ala Asn
                1               5                  10 tgg att aag ggc tca gct ttg gct gat gtg atg aaa aag gct tca gaa      279
Trp Ile Lys Gly Ser Ala Leu Ala Asp Val Met Lys Lys Ala Ser Glu
         15                  20                  25 ctc caa aag aaa ggg gta aag cta att tct ctc gca gct gga gat cca      327
Leu Gln Lys Lys Gly Val Lys Leu Ile Ser Leu Ala Ala Gly Asp Pro
     30                  35                  40 gat ccg gag tta att cca aga gct gtt ctt ggg gaa ata gca aaa gaa      375
Asp Pro Glu Leu Ile Pro Arg Ala Val Leu Gly Glu Ile Ala Lys Glu
 45                  50                  55                  60 gtt ctt gaa aag gaa cca aaa tcc gtt atg tat act ccg gca aat gga      423
Val Leu Glu Lys Glu Pro Lys Ser Val Met Tyr Thr Pro Ala Asn Gly
                 65                  70                  75 atc ccg gag ctt agg gaa gag ctg gca gca ttc ttg aaa aaa tac gac      471
Ile Pro Glu Leu Arg Glu Glu Leu Ala Ala Phe Leu Lys Lys Tyr Asp
             80                  85                  90 cat tta gaa gtt tct cca gaa aac att gtt att aca ata gga gga acg      519
His Leu Glu Val Ser Pro Glu Asn Ile Val Ile Thr Ile Gly Gly Thr
         95                 100                 105 gga gca ttg gat ctt ctt gga agg gtt ttg ata gac cct gga gat gtc      567
Gly Ala Leu Asp Leu Leu Gly Arg Val Leu Ile Asp Pro Gly Asp Val
    110                 115                 120 gtg ata aca gag aac cca tcg tac ata aac aca tta ttg gca ttt gaa      615
Val Ile Thr Glu Asn Pro Ser Tyr Ile Asn Thr Leu Leu Ala Phe Glu
125                 130                 135                 140 cag ttg gga gcc aaa att gag ggg gtt cca gtt gat aac gat ggg atg      663
Gln Leu Gly Ala Lys Ile Glu Gly Val Pro Val Asp Asn Asp Gly Met
                145                 150                 155 agg gtt gat ctg ttg gag gag aaa ata aag gag ctt aaa gct aaa gga      711
Arg Val Asp Leu Leu Glu Glu Lys Ile Lys Glu Leu Lys Ala Lys Gly
            160                 165                 170 cag aaa gtt aag ctg atc tac acc atc ccg act ggt cag aat cca atg      759
Gln Lys Val Lys Leu Ile Tyr Thr Ile Pro Thr Gly Gln Asn Pro Met
        175                 180                 185 ggc gtc act atg agc atg gaa cgg aga aag gca cta ctt gag att gcc      807
Gly Val Thr Met Ser Met Glu Arg Arg Lys Ala Leu Leu Glu Ile Ala
    190                 195                 200 tct aaa tac gac ctc cta ata att gag gac act gct tat aat ttc atg      855
Ser Lys Tyr Asp Leu Leu Ile Ile Glu Asp Thr Ala Tyr Asn Phe Met
205                 210                 215                 220 aga tat gaa gga ggg gat ata gtc ccc tta aag gct ttg gac aat gaa      903
Arg Tyr Glu Gly Gly Asp Ile Val Pro Leu Lys Ala Leu Asp Asn Glu
                225                 230                 235
```

```
gga aga gtt atc gtg gcg gga acg ctc agc aaa gtc ctt gga aca gga      951
Gly Arg Val Ile Val Ala Gly Thr Leu Ser Lys Val Leu Gly Thr Gly
        240                 245                 250 ttc aga att gga tgg ata ata gca gag gga gaa atc ctc aaa aaa gtt      999
Phe Arg Ile Gly Trp Ile Ile Ala Glu Gly Glu Ile Leu Lys Lys Val
            255                 260                 265 ctc atg cag aaa cag cca att gac ttc tgt gct cca gct att tcc caa     1047
Leu Met Gln Lys Gln Pro Ile Asp Phe Cys Ala Pro Ala Ile Ser Gln
    270                 275                 280 tac att gcc cta gaa tac tta aag agg ggc tat ttt gag aag tat cac     1095
Tyr Ile Ala Leu Glu Tyr Leu Lys Arg Gly Tyr Phe Glu Lys Tyr His
285                 290                 295                 300 ttg gaa gga gca ctg ctc ggt tat aaa gag aag agg gac atc atg ctg     1143
Leu Glu Gly Ala Leu Leu Gly Tyr Lys Glu Lys Arg Asp Ile Met Leu
                305                 310                 315 aag gct ctt gaa aat cac ttg cca aat gca gaa ttt aca aag cca ata     1191
Lys Ala Leu Glu Asn His Leu Pro Asn Ala Glu Phe Thr Lys Pro Ile
            320                 325                 330 gcg gga atg ttt gtt atg ttt ttc ctt cca gag gga gca gat ggc atc     1239
Ala Gly Met Phe Val Met Phe Phe Leu Pro Glu Gly Ala Asp Gly Ile
        335                 340                 345 tca ttt gcc aac gag ctc atg gaa agg gag gga gtt gtg gta gtt cca     1287
Ser Phe Ala Asn Glu Leu Met Glu Arg Glu Gly Val Val Val Val Pro
    350                 355                 360 gga aag cct ttc tac aca gac gag tct gga aag aat gct ata agg ctt     1335
Gly Lys Pro Phe Tyr Thr Asp Glu Ser Gly Lys Asn Ala Ile Arg Leu
365                 370                 375                 380 aac ttc tca agg cca agc aag gaa gaa att cca ata gga atc aag aaa     1383
Asn Phe Ser Arg Pro Ser Lys Glu Glu Ile Pro Ile Gly Ile Lys Lys
                385                 390                 395 ctt gct aag ctt tat aag gaa aag ttt ggc gag tga attctttgtt          1429
Leu Ala Lys Leu Tyr Lys Glu Lys Phe Gly Glu
            400                 405 tttacattt cttctgggcc atcacattct cgatggagag aaggttagtt tgttttaat     1489 gcactcagaa aagttctttt tggtgcgggg gcggggattt gaaccccgga accccctacgg  1549 gacgggaccc tcaatcccgc gcctttgacc aggctcggca accccgcaa gagcgccgtt    1609 tatttgtctt cttagtttgt ttataaattt ttctgtcccc tttaaccggg gcgtgtttat   1669
agtaaccttt attagggttt ttgctgaatt cttcaggtg gttgtcgtga tccccagatg    1729
ggatcacaaa ctcaaagacc ctgaaagcgt ggcattcata atcctcgacg ttttagcaga   1789
cttcgaatca gaaggaaagc tgaagaacct gccaaaaatc caaaaatttt ccagtaaaaa   1849
caatactggc aatactcctc tttaaacaat actacaacct acccctcaga gacgccagc    1909 actacggcag aaaattcttc ggagcaaaca ttcactactc aaccctccac aactgggaga   1969
aaaagctgaa cctcgaagaa ctgacaaacc acctcctgaa aaaactccag aaattaccct   2029
acgccagcac tcaagcagac tcaaccatta tcacaaataa aaaaaggaca gaatagaagt   2089
tcaggcaata acgagaatcc tgccgggttt actgtatccg gttgctgtga agatcacaac   2149
ttctgagaac gagctgattg aactcctgcc ggagggttct gggaattttt atgctgatgg   2209
ggcttatgat tcaagaaaag ttctgaacac tgtggtggaa aagggttatc ggccgattgt   2269
taagaaaact aagaaccctc caggtggttt tggtagtaag aagagagata gagtgttttc   2329
tgaagaagag tacaggcata ggaatcctca tgagggggttc tggggtgcgt ttacaacgtg  2389
gtttggcagt aggatcc                                                  2406
```

```
<210> SEQ ID NO 8
<211> LENGTH: 407
<212> TYPE: PRT
<213> ORGANISM: Thermococcus litoralis

<400> SEQUENCE: 8

Met Asp Tyr Thr Lys Tyr Leu Ala Gly Arg Ala Asn Trp Ile Lys Gly
1               5                   10                  15

Ser Ala Leu Ala Asp Val Met Lys Lys Ala Ser Glu Leu Gln Lys Lys
            20                  25                  30

Gly Val Lys Leu Ile Ser Leu Ala Ala Gly Asp Pro Asp Pro Glu Leu
        35                  40                  45

Ile Pro Arg Ala Val Leu Gly Glu Ile Ala Lys Glu Val Leu Glu Lys
50                  55                  60

Glu Pro Lys Ser Val Met Tyr Thr Pro Ala Asn Gly Ile Pro Glu Leu
65                  70                  75                  80

Arg Glu Glu Leu Ala Ala Phe Leu Lys Lys Tyr Asp His Leu Glu Val
                85                  90                  95

Ser Pro Glu Asn Ile Val Ile Thr Ile Gly Thr Gly Ala Leu Asp
            100                 105                 110

Leu Leu Gly Arg Val Leu Ile Asp Pro Gly Asp Val Ile Thr Glu
        115                 120                 125

Asn Pro Ser Tyr Ile Asn Thr Leu Leu Ala Phe Glu Gln Leu Gly Ala
130                 135                 140

Lys Ile Glu Gly Val Pro Val Asp Asn Asp Gly Met Arg Val Asp Leu
145                 150                 155                 160

Leu Glu Glu Lys Ile Lys Glu Leu Lys Ala Lys Gly Gln Lys Val Lys
                165                 170                 175

Leu Ile Tyr Thr Ile Pro Thr Gly Gln Asn Pro Met Gly Val Thr Met
            180                 185                 190

Ser Met Glu Arg Arg Lys Ala Leu Leu Glu Ile Ala Ser Lys Tyr Asp
        195                 200                 205

Leu Leu Ile Ile Glu Asp Thr Ala Tyr Asn Phe Met Arg Tyr Glu Gly
210                 215                 220

Gly Asp Ile Val Pro Leu Lys Ala Leu Asp Asn Glu Gly Arg Val Ile
225                 230                 235                 240

Val Ala Gly Thr Leu Ser Lys Val Leu Gly Thr Gly Phe Arg Ile Gly
                245                 250                 255

Trp Ile Ile Ala Glu Gly Glu Ile Leu Lys Lys Val Leu Met Gln Lys
            260                 265                 270

Gln Pro Ile Asp Phe Cys Ala Pro Ala Ile Ser Gln Tyr Ile Ala Leu
        275                 280                 285

Glu Tyr Leu Lys Arg Gly Tyr Phe Glu Lys Tyr His Leu Glu Gly Ala
290                 295                 300

Leu Leu Gly Tyr Lys Glu Lys Arg Asp Ile Met Leu Lys Ala Leu Glu
305                 310                 315                 320

Asn His Leu Pro Asn Ala Glu Phe Thr Lys Pro Ile Ala Gly Met Phe
                325                 330                 335

Val Met Phe Phe Leu Pro Glu Gly Ala Asp Gly Ile Ser Phe Ala Asn
            340                 345                 350

Glu Leu Met Glu Arg Glu Gly Val Val Val Pro Gly Lys Pro Phe
        355                 360                 365

Tyr Thr Asp Glu Ser Gly Lys Asn Ala Ile Arg Leu Asn Phe Ser Arg
370                 375                 380
```

Pro Ser Lys Glu Glu Ile Pro Ile Gly Ile Lys Lys Leu Ala Lys Leu
385                 390                 395                 400

Tyr Lys Glu Lys Phe Gly Glu
                405

<210> SEQ ID NO 9
<211> LENGTH: 1338
<212> TYPE: DNA
<213> ORGANISM: Artificial Sequence
<220> FEATURE:
<223> OTHER INFORMATION: construct pEX-A258-AGT_T1_opt_RBS

<400> SEQUENCE: 9

```
ggtctcccaa gcttgcatgc ctgcaggtcg actctagagg atccgacgtc aggaaaggag      60
aggattgatg gactatacca atatcttgc gggccgggct aattggatta agggctctgc     120
actcgcggac gtaatgaaaa agcatccga attgcagaaa aagggcgtca aacttatttc     180
gctcgccgcc ggtgatcctg accccgaact gattccccgt gcagtgttgg gcagagattgc    240
aaaggaggtc ctcgaaaaag aacctaagtc ggtaatgtac actcccgcca acggcattcc    300
ggagcttcgg gaggagttgg ccgctttct caagaagtat gaccaccttg aagtgtctcc    360
tgagaacatc gtcatcacca ttggcggtac tggtgcactc gatctgcttg acgtgtact    420
gatcgatcct ggcgacgtag tcatcacgga aaatccatcg tacattaaca ccctcctcgc    480
tttcgaacaa ctcggagcaa aaattgaggg agtaccggtg ataacgacg gcatgcgggt    540
tgaccttctg gaagagaaga tcaaagagtt gaaggctaag ggtcaaaaag tgaaactgat    600
ttatacgatt ccaaccggac aaaatccaat gggtgtaacg atgtcaatgg aacggcgtaa    660
ggcgttgctg gagatcgcct caaaatacga tttgctgatc attgaggaca ctgcgtacaa    720
cttcatgcgg tacgaaggtg gtgatattgt cccgctcaag gcgttggata tgagggacg    780
tgtgatcgtg gccggaaccc tttcaaaggt actcggcact ggttttcgta ttggctggat    840
tatcgccgaa ggcgagattt tgaagaaggt tctcatgcag aaacaaccta tcgatttctg    900
cgcgcccgcg atttcgcagt atattgcgct cgaatatctg aagcgtggat acttcgagaa    960
gtaccacctt gagggtgcat tgtgggata taaggagaaa cgcgacatca tgctgaaggc   1020
ccttgagaat catctcccga acgcagaatt caccaagccc atcgcgggta tgttcgtcat   1080
gttcttcctg ccagaaggtg cggacggcat ctcctttgcg aacgagctca tggagcgcga   1140
gggcgtagtc gttgtccccg gaaaaccttt ctacactgac gaatccggta aaaacgccat   1200
tcggctgaat ttctcccgcc cttcaaaaga agagattccc attggaatta aaaaacttgc   1260
taaactgtat aaagaaaaat tcggtgagta ataaggatcc ccgggtaccg agctcgaatt   1320
cactggccgt cggagacc                                                  1338
```

<210> SEQ ID NO 10
<211> LENGTH: 1146
<212> TYPE: DNA
<213> ORGANISM: Moorea producens
<220> FEATURE:
<221> NAME/KEY: CDS
<222> LOCATION: (1)..(1143)

<400> SEQUENCE: 10 atg tcg gaa aaa att gtt aat tcc tgg aat gaa tgg gat gaa ttg gaa       48
Met Ser Glu Lys Ile Val Asn Ser Trp Asn Glu Trp Asp Glu Leu Glu
1               5                   10                  15 gaa atg gtg gta gga att gca gac tat gct agc ttt gaa cca aaa gaa       96

```
                Glu Met Val Val Gly Ile Ala Asp Tyr Ala Ser Phe Glu Pro Lys Glu
                             20                  25                  30 cca ggg aat cat ccg aaa tta aga aat caa aat tta gcg gaa atc att            144
Pro Gly Asn His Pro Lys Leu Arg Asn Gln Asn Leu Ala Glu Ile Ile
            35                  40                  45 cct ttc ccc agt gga cct aaa gac cct aaa gtc ctt gaa aaa gct aat            192
Pro Phe Pro Ser Gly Pro Lys Asp Pro Lys Val Leu Glu Lys Ala Asn
 50                  55                  60 gaa gaa tta aat gga ctg gct tat tta tta aaa gac cac gat gtg ata            240
Glu Glu Leu Asn Gly Leu Ala Tyr Leu Leu Lys Asp His Asp Val Ile
 65                  70                  75                  80 gta aga aga ccc gaa aaa att gat ttt act aaa tct cta aaa aca cct            288
Val Arg Arg Pro Glu Lys Ile Asp Phe Thr Lys Ser Leu Lys Thr Pro
                 85                  90                  95 tac ttt gaa gtt gca aat caa tac tgt gga gtc tgt cct cgg gat gtc            336
Tyr Phe Glu Val Ala Asn Gln Tyr Cys Gly Val Cys Pro Arg Asp Val
            100                 105                 110 atg att acc ttt ggg aat gaa atc atg gaa gcg act atg tcg aag aga            384
Met Ile Thr Phe Gly Asn Glu Ile Met Glu Ala Thr Met Ser Lys Arg
            115                 120                 125 gct aga ttt ttt gaa tac tta cct tac cgg aaa ttg gtc tat gaa tat            432
Ala Arg Phe Phe Glu Tyr Leu Pro Tyr Arg Lys Leu Val Tyr Glu Tyr
130                 135                 140 tgg aat aaa gac gag cat atg att tgg aat gct gcg cct aaa ccg act            480
Trp Asn Lys Asp Glu His Met Ile Trp Asn Ala Ala Pro Lys Pro Thr
145                 150                 155                 160 atg cag gat agt atg tat cta gag aat ttc tgg gag ctg tct tta gaa            528
Met Gln Asp Ser Met Tyr Leu Glu Asn Phe Trp Glu Leu Ser Leu Glu
                165                 170                 175 gaa cga ttt aag cgt atg cat gat ttt gaa ttt tgt att aca caa gat            576
Glu Arg Phe Lys Arg Met His Asp Phe Glu Phe Cys Ile Thr Gln Asp
            180                 185                 190 gaa gta att ttt gat gcg gct gac tgt agc aga tta gga aag gat ata            624
Glu Val Ile Phe Asp Ala Ala Asp Cys Ser Arg Leu Gly Lys Asp Ile
            195                 200                 205 tta gtt cag gaa tcg atg aca aca aat aga aca gga att cgg tgg tta            672
Leu Val Gln Glu Ser Met Thr Thr Asn Arg Thr Gly Ile Arg Trp Leu
210                 215                 220 aaa aag cac cta gaa cca aga gga ttt cgg gtt cac cct gtt cat ttt            720
Lys Lys His Leu Glu Pro Arg Gly Phe Arg Val His Pro Val His Phe
225                 230                 235                 240 ccc ctt gat ttt ttc ccc tca cac att gac tgt acg ttt gtt cct ttg            768
Pro Leu Asp Phe Phe Pro Ser His Ile Asp Cys Thr Phe Val Pro Leu
                245                 250                 255 cga cca ggt ctt att ttg aca aac cct gaa aga cct ata cgg gaa gag            816
Arg Pro Gly Leu Ile Leu Thr Asn Pro Glu Arg Pro Ile Arg Glu Glu
            260                 265                 270 gag gag aag att ttt aaa gag aat ggc tgg gag ttg atc aca gtt cct            864
Glu Glu Lys Ile Phe Lys Glu Asn Gly Trp Glu Leu Ile Thr Val Pro
            275                 280                 285 caa ccg act tgc tcg aat gat gaa atg cca atg ttt tgc cag tcc agt            912
Gln Pro Thr Cys Ser Asn Asp Glu Met Pro Met Phe Cys Gln Ser Ser
            290                 295                 300 aag tgg ttg tca atg aat gtt ctg agt ata tca ccg aca aag gtt atc            960
Lys Trp Leu Ser Met Asn Val Leu Ser Ile Ser Pro Thr Lys Val Ile
305                 310                 315                 320 tgt gag gaa aga gaa aaa cct ctc caa gaa ttg ttg gat aag cat gga           1008
Cys Glu Glu Arg Glu Lys Pro Leu Gln Glu Leu Leu Asp Lys His Gly
                325                 330                 335
```

```
ttt gag gtt ttt cct tta ccc ttt aga cat gtc ttt gaa ttt ggg ggg       1056
Phe Glu Val Phe Pro Leu Pro Phe Arg His Val Phe Glu Phe Gly Gly
            340                 345                 350 tct ttt cat tgt gca act tgg gat att cgc cga aaa ggt gag tgt gaa       1104
Ser Phe His Cys Ala Thr Trp Asp Ile Arg Arg Lys Gly Glu Cys Glu
        355                 360                 365 gat tat tta cca aat tta aac tat caa ccg att tgt ggt taa               1146
Asp Tyr Leu Pro Asn Leu Asn Tyr Gln Pro Ile Cys Gly
370                 375                 380
```

<210> SEQ ID NO 11
<211> LENGTH: 381
<212> TYPE: PRT
<213> ORGANISM: Moorea producens

<400> SEQUENCE: 11

```
Met Ser Glu Lys Ile Val Asn Ser Trp Asn Glu Trp Asp Glu Leu Glu
1               5                   10                  15

Glu Met Val Val Gly Ile Ala Asp Tyr Ala Ser Phe Glu Pro Lys Glu
            20                  25                  30

Pro Gly Asn His Pro Lys Leu Arg Asn Gln Asn Leu Ala Glu Ile Ile
        35                  40                  45

Pro Phe Pro Ser Gly Pro Lys Asp Pro Lys Val Leu Glu Lys Ala Asn
    50                  55                  60

Glu Glu Leu Asn Gly Leu Ala Tyr Leu Leu Lys Asp His Asp Val Ile
65                  70                  75                  80

Val Arg Arg Pro Glu Lys Ile Asp Phe Thr Lys Ser Leu Lys Thr Pro
                85                  90                  95

Tyr Phe Glu Val Ala Asn Gln Tyr Cys Gly Val Cys Pro Arg Asp Val
            100                 105                 110

Met Ile Thr Phe Gly Asn Glu Ile Met Glu Ala Thr Met Ser Lys Arg
        115                 120                 125

Ala Arg Phe Phe Glu Tyr Leu Pro Tyr Arg Lys Leu Val Tyr Glu Tyr
    130                 135                 140

Trp Asn Lys Asp Glu His Met Ile Trp Asn Ala Ala Pro Lys Pro Thr
145                 150                 155                 160

Met Gln Asp Ser Met Tyr Leu Glu Asn Phe Trp Glu Leu Ser Leu Glu
                165                 170                 175

Glu Arg Phe Lys Arg Met His Asp Phe Glu Phe Cys Ile Thr Gln Asp
            180                 185                 190

Glu Val Ile Phe Asp Ala Ala Asp Cys Ser Arg Leu Gly Lys Asp Ile
        195                 200                 205

Leu Val Gln Glu Ser Met Thr Thr Asn Arg Thr Gly Ile Arg Trp Leu
    210                 215                 220

Lys Lys His Leu Glu Pro Arg Gly Phe Arg Val His Pro Val His Phe
225                 230                 235                 240

Pro Leu Asp Phe Pro Ser His Ile Asp Cys Thr Phe Val Pro Leu
                245                 250                 255

Arg Pro Gly Leu Ile Leu Thr Asn Pro Glu Arg Pro Ile Arg Glu Glu
            260                 265                 270

Glu Glu Lys Ile Phe Lys Glu Asn Gly Trp Glu Leu Ile Thr Val Pro
        275                 280                 285

Gln Pro Thr Cys Ser Asn Asp Glu Met Pro Met Phe Cys Gln Ser Ser
    290                 295                 300

Lys Trp Leu Ser Met Asn Val Leu Ser Ile Ser Pro Thr Lys Val Ile
305                 310                 315                 320
```

```
Cys Glu Glu Arg Glu Lys Pro Leu Gln Glu Leu Leu Asp Lys His Gly
            325                 330                 335

Phe Glu Val Phe Pro Leu Pro Phe Arg His Val Phe Glu Phe Gly Gly
            340                 345                 350

Ser Phe His Cys Ala Thr Trp Asp Ile Arg Arg Lys Gly Glu Cys Glu
        355                 360                 365

Asp Tyr Leu Pro Asn Leu Asn Tyr Gln Pro Ile Cys Gly
    370                 375                 380

<210> SEQ ID NO 12
<211> LENGTH: 1248
<212> TYPE: DNA
<213> ORGANISM: Artificial Sequence
<220> FEATURE:
<223> OTHER INFORMATION: construct pMA-T_AGAT_Mp

<400> SEQUENCE: 12
cgtctctgtg gataactgag cggataagtt cctagtacgc gtgcgagcag gaagaacatg      60
agcgagaaaa ttgtgaacag ctggaatgaa tgggatgaac tggaagaaat ggttgttggt     120
attgcagatt atgcaagctt tgaaccgaaa gaaccgggta atcatccgaa actgcgtaat     180
cagaatctgg cagaaattat tccgtttccg agcggtccga agatccgaa agttctggaa      240 aaagcaaatg aagaactgaa tggtctggcc tatctgctga agatcatga tgttattgtt      300 cgccgtccgg aaaaaatcga ctttaccaaa agcctgaaaa ccccgtattt cgaagttgcc    360
aatcagtatt gtggtgtttg tccgcgtgat gttatgatta cctttggcaa cgaaattatg    420
gaagccacca tgagcaaacg tgcccgtttt tttgaatatc tgccgtatcg taaactggtg    480
tatgagtatt ggaacaaaga tgagcatatg atctggaatg cagcaccgaa accgaccatg   540
caggatagca tgtatctgga aaacttttgg gaactgagcc tggaagaacg tttttaaacgt  600 atgcacgatt ttgagttttg catcacccag gatgaagtga ttttttgatgc agcagattgt    660 agccgtctgg gtaaagatat tctggttcaa gaaagcatga ccaccaatcg taccggtatt   720
cgttggctga aaaaacatct ggaaccgcgt ggttttcgtg ttcatccggt tcattttccg    780
ctggattttt ttccgagcca tattgattgt accttttgttc cgctgcgtcc gggtctgatt    840
ctgaccaatc cggaacgtcc gattcgtgaa gaagaagaga aaatcttcaa agagaatggc   900
tgggagctga ttaccgttcc gcagccgacc tgtagcaatg atgaaatgcc gatgttttgt   960
cagagcagca atggctgag catgaatgtt ctgagcatta gcccgaccaa agttatttgt  1020
gaagaacgtg aaaaaccgct gcaagaactg ctggataaac atggttttga agtgtttccg  1080
ctgccgtttc gtcatgtttt tgaatttggt ggtagctttc attgtgccac ctgggatatt   1140
cgtcgtaaag gtgaatgtga agattatctg ccgaatctga attatcagcc gatttgtggt  1200
taataagacg tccgcgaggg ccgtgttgcc ggtttcttca gagagacg                1248

<210> SEQ ID NO 13
<211> LENGTH: 46
<212> TYPE: DNA
<213> ORGANISM: Artificial Sequence
<220> FEATURE:
<223> OTHER INFORMATION: construct PsodcarAB-LA-F

<400> SEQUENCE: 13
ggaaacagct atgacatgat tacgcggtta tcgcggaatc cgtatg                    46

<210> SEQ ID NO 14
```

-continued

<211> LENGTH: 25
<212> TYPE: DNA
<213> ORGANISM: Artificial Sequence
<220> FEATURE:
<223> OTHER INFORMATION: construct PsodcarAB-LA-R

<400> SEQUENCE: 14
ttaagcgttt tgtgcaactc cgtct                                    25

<210> SEQ ID NO 15
<211> LENGTH: 50
<212> TYPE: DNA
<213> ORGANISM: Artificial Sequence
<220> FEATURE:
<223> OTHER INFORMATION: construct PsodcarAB-F

<400> SEQUENCE: 15
agacggagtt gcacaaaacg cttaaaccct acttagctgc caattattcc         50

<210> SEQ ID NO 16
<211> LENGTH: 50
<212> TYPE: DNA
<213> ORGANISM: Artificial Sequence
<220> FEATURE:
<223> OTHER INFORMATION: construct PsodcarAB-R

<400> SEQUENCE: 16
ggtaggtggt ggtgtcttta ctcatgggta aaaatccttt cgtaggttt          50

<210> SEQ ID NO 17
<211> LENGTH: 25
<212> TYPE: DNA
<213> ORGANISM: Artificial Sequence
<220> FEATURE:
<223> OTHER INFORMATION: construct PsodcarAB-RA-F

<400> SEQUENCE: 17
atgagtaaag acaccaccac ctacc                                    25

<210> SEQ ID NO 18
<211> LENGTH: 46
<212> TYPE: DNA
<213> ORGANISM: Artificial Sequence
<220> FEATURE:
<223> OTHER INFORMATION: construct PsodcarAB-RA-R

<400> SEQUENCE: 18
gttgtaaaac gacggccagt gccaccggtg atgtggttct tcactg             46

<210> SEQ ID NO 19
<211> LENGTH: 51
<212> TYPE: DNA
<213> ORGANISM: Artificial Sequence
<220> FEATURE:
<223> OTHER INFORMATION: construct 1f-aceB-D2_vec

<400> SEQUENCE: 19
gaattcgagc tcggtacccg gggatcctct ttcatacctt aacgcagtag t       51

<210> SEQ ID NO 20
<211> LENGTH: 37
<212> TYPE: DNA
<213> ORGANISM: Artificial Sequence
<220> FEATURE:
<223> OTHER INFORMATION: construct 1r-aceB-D2_aceB

<400> SEQUENCE: 20

```
gcgttgacgc gggctcgagc agtggtcgtc gacaagc                              37

<210> SEQ ID NO 21
<211> LENGTH: 37
<212> TYPE: DNA
<213> ORGANISM: Artificial Sequence
<220> FEATURE:
<223> OTHER INFORMATION: construct 2f-aceB-D2_aceB

<400> SEQUENCE: 21
cgacgaccac tgctcgagcc cgcgtcaacg cgttcgg                              37

<210> SEQ ID NO 22
<211> LENGTH: 48
<212> TYPE: DNA
<213> ORGANISM: Artificial Sequence
<220> FEATURE:
<223> OTHER INFORMATION: construct 2r-aceB_D2_Vec

<400> SEQUENCE: 22
caagcttgca tgcctgcagg tcgactttgg aacggagttc gctgggta                  48

<210> SEQ ID NO 23
<211> LENGTH: 17
<212> TYPE: DNA
<213> ORGANISM: Artificial Sequence
<220> FEATURE:
<223> OTHER INFORMATION: Shine-Dalgarno-Sequenz; Shi F, Luan M, Li Y,
      AMB Express. 2018 Apr 18;8(1):61. doi: 10.1186/s13568-018-0595-2

<400> SEQUENCE: 23
aggaaaggag aggattg                                                    17
```